United States Patent
Duffy

(10) Patent No.: US 12,036,219 B2
(45) Date of Patent: Jul. 16, 2024

(54) METHODS OF TREATING INFECTIONS IN OVERWEIGHT AND OBESE PATIENTS USING ANTIBIOTICS

(71) Applicant: Melinta Subsidiary Corp., Parsippany, NJ (US)

(72) Inventor: Erin M. Duffy, Deep River, CT (US)

(73) Assignee: MELINTA SUBSIDIARY CORP., Parsippany, NJ (US)

( * ) Notice: Subject to any disclaimer, the term of this patent is extended or adjusted under 35 U.S.C. 154(b) by 80 days.

(21) Appl. No.: 14/775,465

(22) PCT Filed: Mar. 14, 2014

(86) PCT No.: PCT/US2014/027220
§ 371 (c)(1),
(2) Date: Sep. 11, 2015

(87) PCT Pub. No.: WO2014/152332
PCT Pub. Date: Sep. 25, 2014

(65) Prior Publication Data
US 2016/0058750 A1 Mar. 3, 2016

Related U.S. Application Data

(60) Provisional application No. 61/790,179, filed on Mar. 15, 2013.

(51) Int. Cl.
| | | |
|---|---|---|
| *A61K 31/4709* | (2006.01) | |
| *A61K 9/00* | (2006.01) | |
| *A61K 9/19* | (2006.01) | |
| *A61K 9/20* | (2006.01) | |
| *A61K 31/133* | (2006.01) | |
| *A61K 47/18* | (2017.01) | |
| *A61K 47/26* | (2006.01) | |
| *A61K 47/40* | (2006.01) | |

(52) U.S. Cl.
CPC ........ *A61K 31/4709* (2013.01); *A61K 9/0019* (2013.01); *A61K 9/2013* (2013.01); *A61K 9/2027* (2013.01); *A61K 9/2054* (2013.01); *A61K 31/133* (2013.01); *A61K 47/183* (2013.01); *A61K 47/26* (2013.01); *A61K 47/40* (2013.01)

(58) Field of Classification Search
CPC .............. A61K 31/133; A61K 31/4709; A61K 2300/00; A61K 9/0019; A61K 9/2013; A61K 9/2027; A61K 9/2054
USPC ..................................................... 514/210.21
See application file for complete search history.

(56) References Cited

U.S. PATENT DOCUMENTS

| | | |
|---|---|---|
| 4,399,134 A | 8/1983 | Ishikawa et al. |
| 4,552,879 A | 11/1985 | Ishikawa et al. |
| 4,980,470 A | 12/1990 | Masuzawa et al. |
| 4,990,517 A | 2/1991 | Petersen et al. |
| 5,053,407 A | 10/1991 | Hayakawa et al. |
| 5,607,942 A | 3/1997 | Petersen et al. |
| 5,633,262 A | 5/1997 | Hong et al. |
| 5,654,435 A | 8/1997 | Barbachyn et al. |
| 5,688,792 A | 11/1997 | Barbachyn et al. |
| 5,776,944 A | 7/1998 | Hong et al. |
| 5,840,684 A | 11/1998 | Cooper et al. |
| 5,843,889 A | 12/1998 | Cooper et al. |
| 5,849,752 A | 12/1998 | Grunenberg et al. |
| 5,880,283 A | 3/1999 | Matsumoto et al. |
| 5,912,226 A | 6/1999 | Baker et al. |
| 5,935,952 A | 8/1999 | Todo et al. |
| 5,939,382 A | 8/1999 | Berglund et al. |
| 5,952,466 A | 9/1999 | Berglund et al. |
| 5,962,468 A | 10/1999 | Hong et al. |
| 5,977,062 A | 11/1999 | Cooper et al. |
| 5,994,297 A | 11/1999 | Nicas et al. |
| 5,998,436 A | 12/1999 | Yazaki et al. |
| 5,998,581 A | 12/1999 | Berglund et al. |
| 6,025,370 A | 2/2000 | Todo et al. |
| 6,133,284 A | 10/2000 | Yazaki et al. |
| 6,156,903 A | 12/2000 | Yazaki et al. |
| 6,262,071 B1 | 7/2001 | Crabb et al. |
| 6,331,550 B1 | 12/2001 | Citron et al. |

(Continued)

FOREIGN PATENT DOCUMENTS

| | | |
|---|---|---|
| JP | 2002201191 A | 7/2002 |
| JP | 2002255962 A | 9/2002 |

(Continued)

OTHER PUBLICATIONS

Roe et al. Underdosing of common antibiotics for obese patients in the ED. American Journal of Emergency Medicine (2012) 30, 1212-1214.*
O'Riordan et al. Results of a phase 2 study comparing two doses of delafloxacin to tigecycline in adults with complicated skin and skin-structure infections. Clinical Microbiology and Infections (May 2009) vol. 15, Suppl. S4, S519, abstract No. p. 1794, ISSN: 1198-743x.*
Barbachyn, et al., "Oxazolidinone Structure-Activity Relationships Leading to Linezolid", Angew. Chem. Int. Ed., vol. 42, pp. 2010-2023 (2003).
Bhalodi, et al., "Pharmacokinetics of Intravenous Linezolid in Moderately to Morbidly Obese Adults," Antimicrob Agents Chemother., vol. 57, No. 3, pp. 1144-1149 (Mar. 2013, published online Dec. 17, 2012).

(Continued)

*Primary Examiner* — Jared Barsky
(74) *Attorney, Agent, or Firm* — Wilmer Cutler Pickering Hale and Dorr LLP

(57) ABSTRACT

The present disclosure relates generally to methods of treating infections in overweight or obese patients using antibiotics. According to statistics compiled by National Health and Nutrition Examination Survey conducted by the National Center for Health Statistics (NCHS) of the U.S. Centers for Disease Control and Prevention (CDC), in 2009-2010, 35.7% of adults in the United States were found to be obese. Ogden, C.L. NCHS Data Brief 2012, 82, available at http://www.cdc.gov/nchs/data/databiefs/db82.pdf (last visited Mar. 2, 2013).

5 Claims, 7 Drawing Sheets

(56) References Cited

U.S. PATENT DOCUMENTS

| | | | |
|---|---|---|---|
| 6,340,689 B1 | 1/2002 | Dubois et al. |
| 6,455,540 B1 | 9/2002 | Citron et al. |
| 6,455,669 B1 | 9/2002 | Judice et al. |
| 6,468,967 B1 | 10/2002 | Oleson, Jr. et al. |
| 6,514,986 B2 | 2/2003 | de Souza et al. |
| 6,518,242 B1 | 2/2003 | Chen et al. |
| 6,559,305 B1 | 5/2003 | Bergren |
| 6,589,955 B2 | 7/2003 | Raghavan et al. |
| 6,608,078 B2 | 8/2003 | De Souza et al. |
| 6,620,781 B2 | 9/2003 | Linsell et al. |
| 6,635,618 B2 | 10/2003 | Leadbetter et al. |
| 6,664,267 B1 | 12/2003 | de Souza et al. |
| 6,723,734 B2 | 4/2004 | Kim et al. |
| 6,750,224 B1 | 6/2004 | Patel et al. |
| 6,753,333 B2 | 6/2004 | De Souza et al. |
| 6,770,621 B2 | 8/2004 | Linsell et al. |
| 6,803,376 B1 | 10/2004 | Appelbaum et al. |
| 6,828,299 B2 | 12/2004 | Yang et al. |
| 6,831,150 B2 | 12/2004 | Linsell |
| 6,846,939 B2 | 1/2005 | Nelson et al. |
| 6,852,689 B2 | 2/2005 | Oleson, Jr. et al. |
| 6,858,584 B2 | 2/2005 | Judice et al. |
| 6,872,701 B2 | 3/2005 | Leadbetter et al. |
| 6,872,804 B2 | 3/2005 | Mu |
| 6,878,686 B2 | 4/2005 | Marquess et al. |
| 6,887,976 B2 | 5/2005 | Leadbetter et al. |
| 6,900,225 B2 | 5/2005 | Takemura et al. |
| 6,969,726 B2 | 11/2005 | Lou et al. |
| 7,816,376 B2 | 10/2010 | Schadt et al. |
| 2003/0119848 A1 | 6/2003 | Takemura et al. |
| 2003/0125348 A1 | 7/2003 | Nelson et al. |
| 2003/0166585 A1 | 9/2003 | Draper et al. |
| 2003/0187008 A1 | 10/2003 | Takemura et al. |
| 2004/0038967 A1 | 2/2004 | Kano et al. |
| 2004/0063674 A1 | 4/2004 | Levy et al. |
| 2004/0092490 A1 | 5/2004 | Draper et al. |
| 2004/0142957 A1 | 7/2004 | Takemura et al. |
| 2004/0198715 A1 | 10/2004 | Cavaleri et al. |
| 2004/0214800 A1 | 10/2004 | Levy et al. |
| 2004/0214801 A1 | 10/2004 | Nelson et al. |
| 2004/0220122 A1 | 11/2004 | Cavaleri et al. |
| 2004/0224908 A1 | 11/2004 | Cavaleri et al. |
| 2004/0242548 A1 | 12/2004 | Draper et al. |
| 2005/0004050 A1 | 1/2005 | Stogniew |
| 2005/0026875 A1 | 2/2005 | Nelson et al. |
| 2005/0026876 A1 | 2/2005 | Nelson et al. |
| 2005/0043317 A1 | 2/2005 | Zhou et al. |
| 2005/0070510 A1 | 3/2005 | Draper et al. |
| 2005/0090433 A1 | 4/2005 | Colombo et al. |
| 2005/0153971 A1 | 7/2005 | Chen et al. |
| 2007/0238719 A1 | 10/2007 | Hopkins et al. |
| 2007/0249577 A1 | 10/2007 | Hopkins et al. |
| 2009/0192197 A1 | 7/2009 | Rhee et al. |
| 2012/0065186 A1 | 3/2012 | Li et al. |

FOREIGN PATENT DOCUMENTS

| | | | |
|---|---|---|---|
| JP | 2003096075 A | 4/2003 |
| JP | 2004244380 A | 9/2004 |
| WO | WO-9630401 A1 | 10/1996 |
| WO | WO-97/11068 A1 | 3/1997 |
| WO | WO-9821952 A1 | 5/1998 |
| WO | WO-9822121 A1 | 5/1998 |
| WO | WO-9910006 A1 | 3/1999 |
| WO | WO-00018419 A2 | 4/2000 |
| WO | WO-0066144 A2 | 11/2000 |
| WO | WO-01/34595 A1 | 5/2001 |
| WO | WO-2001/058876 A1 | 8/2001 |
| WO | WO-01072738 A1 | 10/2001 |
| WO | WO-01081350 A1 | 11/2001 |
| WO | WO-01094342 A1 | 12/2001 |
| WO | WO-2002/04406 A2 | 1/2002 |
| WO | WO-2002/042312 A1 | 5/2002 |
| WO | WO-02072031 A2 | 9/2002 |
| WO | WO-03005971 A2 | 1/2003 |
| WO | WO-03029270 A2 | 4/2003 |
| WO | WO-2003/076428 A1 | 9/2003 |
| WO | WO-03075857 A2 | 9/2003 |
| WO | WO-2004038000 A2 | 5/2004 |
| WO | WO-2004038001 A2 | 5/2004 |
| WO | WO-2004055027 A1 | 7/2004 |
| WO | WO-2004058261 A1 | 7/2004 |
| WO | WO-2004058886 A1 | 7/2004 |
| WO | WO-2004064728 A2 | 8/2004 |
| WO | WO-2004091513 A2 | 10/2004 |
| WO | WO-2005009944 A1 | 2/2005 |
| WO | WO-2005012270 A2 | 2/2005 |
| WO | WO-2005012271 A2 | 2/2005 |
| WO | WO-2005019211 A2 | 3/2005 |
| WO | WO-2005061468 A1 | 7/2005 |
| WO | WO-2005070904 A2 | 8/2005 |
| WO | WO-2006015194 A2 | 2/2006 |
| WO | WO-2006022794 A1 | 3/2006 |
| WO | WO-2006042034 A2 | 4/2006 |
| WO | WO-2006110815 A1 | 10/2006 |
| WO | WO-2010/056872 A2 | 5/2010 |
| WO | WO-2010/096551 A2 | 8/2010 |
| WO | WO-2011/146255 | 11/2011 |

OTHER PUBLICATIONS

Candiani, et al., "In-Vitro and In-Vivo Antibacterial Activity of BI 397, a New Semi-Synthetic Glycopeptide Antibiotic," J. Antimicrob. Chemotherapy, vol. 44, pp. 179-192 (1999).

Chagnac, et al., "Glomerular Hemodynamics in Severe Obesity," Am. J. Physiol. Renal. Physiol., vol. 278, pp. F817-F822 (2000).

Falagas, M.E. and Kompoti, M., "Obesity and Infection," Lancet Infect. Dis., vol. 6(7), pp. 438-446 (2006).

Griffin, et al., "Adverse Renal Consequences of Obesity," Am. J. Physiol. Renal. Physiol., vol. 294(4), pp. F685-F696 (2008).

Haight, et al., "Synthesis of the Quinolone ABT-492: Crystallizations for Optimal Processing," Organic Process Research & Development, vol. 10(4), pp. 751-756 (2006).

Hanley, et al., "Effect of Obesity on the Pharmacokinetics of Drugs in Humans," Clin. Pharmacokinetics, vol. 49(2), pp. 71-87 (2010).

International Search Report and Written Opinion issued by the U.S. Patent and Trademark Office as International Searching Authority for International Application No. PCT/US2014/027220 dated Jul. 21, 2014 (14 pgs.).

Kurazono, et al., "In Vitro Activities of ME1036 (CP5609), a Novel Parenteral Carbapenem, against Methicillin-Resistant Staphylococci," Antimicrobial Agents and Chemotherapy, vol. 48, No. 8, pp. 2831-2837 (Aug. 2004).

London, S. "Telavancin Adds Option for Obese Patients with SSSIs," Dermatology News, Available at <http://www.edermatologynews.com/news/print-friendly/telavancin-adds-option-for-obese-patients-with-sssis/8eedc843f6d16d900fd603000ba4937b.html?type=98> (Oct. 18, 2011) (2 pgs.).

Longcor, et al., "Objective Measures of Clinical Efficacy in a Phase 2b Exploratory Study of Delafloxacin Compared to Vancomycin and Linezolid in Adults with Acute Bacterial Skin and Skin Structure Infections (ABSSSI)," 52nd ICAAC, San Francisco, California, Poster L1-1667c (Sep. 9-12, 2012).

Mercier, et al., "Pharmacodynamic Evaluation of a New Glycopeptide, LY333328, and In Vitro Activity against Staphylococcus aureus and Enterococcus faecium", Antimicrobial Agents and Chemotherapy, vol. 41, No. 6, pp. 1307-1312 (Jun. 1997).

No Author, "A Phase 2 Exploratory Study of Objective Endpoints in Subjects with Acute Bacterial Skin and Skin Structure Infections Treated with Delafloxacin, Vancomycin, or Linezolid," Adis Clinical Trials Insight (Feb. 3, 2011) 4 pgs.

Ogden, et al., "Prevalence of Obesity in the United States 2009-2010," NCHS Data Brief, No. 82 (Jan. 2012) (8 pgs.).

Otani et al., "In Vitro and In Vivo antibacterial Activities of DK-507k, a Novel Fluoroquinolone," Antimicrobial Agents and Chemotherapy, vol. 47, No. 12, pp. 3750-3759 (2003).

Pai, et al. "Influence of Morbid Obesity on the Single-Dose Pharmacokinetics of Daptomycin," Antimicrobial Agents Chemother., vol. 51(8), pp. 2741-2747 (2007).

(56) References Cited

OTHER PUBLICATIONS

Reynolds, et al., "Performance of a Vancomycin Dosage Regimen Developed for Obese Patients," Am J Health Syst Pharm, vol. 69, No. 11, pp. 944-950 (Jun. 1, 2012).
Wurtz, et al., "Antimicrobial Dosing in Obese Patients," Clin. Infect. Dis., vol. 25, pp. 112-118 (1997).
Rubino, C., et al., "Population pharmacokinetics and pharmacokinetic-pharmacodynamic metrics for delafloxacin," Clinical Microbiology and Infection, vol. 16, Suppl. 2, 20th ECCMID—Oral Presentations, p. S116, O519 (2010).
O'Riordan, W., et al., "A Comparison of the Efficacy and Safety of Intravenous Followed by Oral Delafloxacin With Vancomycin Plus Aztreonam for the Treatment of Acute Bacterial Skin and Skin Structure Infections: A Phase 3, Multinational, Double-Blind, Randomized Study," Clinical Infectious Diseases, vol. 67, pp. 657-666, published online Mar. 6, 2018.
Remy, J.M., et al., "Activity of delafloxacin against methicillin-resistant *Staphylococcus aureus*: resistance selection and characterization," J. Antimicrob. Chemotherapy vol. 67, pp. 2814-2820 (advance access publication Aug. 8, 2012).
Burak, E., et al., "Pharmacokinetics and Pharmacodynamics of Delafloxacin in *S. aureus* Murine Thigh Infection Models," Rib-X Pharmaceuticals, Inc., New Haven, CT, USA and Independent Consultant, Salem, CT, USA presented 49th ICAAC, San Francisco, CA, USA, Sep. 12-15, 2009—Poster A1-1941 (1 total page).
Lawrence, L. et al., "Metabolism and mass balance of [14C]-Delafloxacin in healthy human volunteers following intravenous administration," Quotient Bioresearch Ltd, Northants, UK and Rib-X Pharmaceuticals, New Haven, USA presented as 52nd ICAAC, Sept. 9-12, 2012—Poster A—1956 (1 total page).
Lemaire, S., et al., "Contrasting Effects of Acidic pH on the Extracellular and Intracellular Activities of the Anti-Gram-Positive Fluoroquinolones Moxifloxacin and Delafloxacin against *Staphylococcus aureus*," Antimicrobial Agents and Chemotherapy, 55(2), pp. 649-658, (2011).
Allard, S., et al., "Intravenous ciprofloxacin disposition in obesity," Clinical Pharmacology and Therapeutics, vol. 54, pp. 368-373 (1993).
Rejection Ruling dated Mar. 11, 2022 by Chilean Industrial Property Institute ("Chilean Patent Office") in Chilean Patent Application No. 2015-002759 with English translation (10 total pages).
Communication pursuant to Article 94(3) EPC dated Apr. 21, 2022 by European Patent Office in European Patent Application No. 14768456.7 (4 total pages).
Technical Examination Report dated Apr. 27, 2022 by Brazilian Patent Office in Brazlian Patent Application No. BR112015023044-0 with English translation (10 total pages).
Office Action dated May 17, 2022 by Turkish Patent Office in Turkish Patent Application No. 2015/14167 with English translation (6 total pages).
Rejection Decision dated Oct. 6, 2022 by Brazilian Patent Office in Brazilian Patent Application No. BR122022014882-4 with English translation (7 total pages).
Rejection Decision dated Nov. 18, 2022 by Brazilian Patent Office in Brazilian Patent Application No. BR112015023044-0 with English translation (8 total pages).
Unfavorable Opinion issued by Brazilian National Institute of Industrial Property in Brazilian Patent Application No. BR112015023044-0 with English translation, Aug. 8, 2022 (12 total pages).
Duffy, E.M., et al., Delafloxacin Chemical Properties Lead to Increased Potency Against Gram-positive Pathogens, Including Quinolone-Resistant Pathogens (II), Poster E-183, 50th ICAAC (Boston, MA, USA), Sep. 12-15, 2010 (1 total page).
Nilius, A.M., "In Vitro Antibacterial Potency and Spectrum of ABT-492, a New Fluoroquinolone," Antimicrobial Agents and Chemotherapy, vol. 47, No. 10, pp. 3260-3269 (Oct. 2003).
Decision on Appeal issued by Grievance Committee of the Cooperation Council for the Arab States of the Gulf ("GCC Patent Office") in Gulf Cooperation Council Patent Application No. 26770 with English translation, Oct. 5, 2022 (48 total pages).
Cook, et al., "Pharmacokinetics of Intravenous Levofloxacin Administered at 750 Milligrams in Obese Adults," Antimicrobial Agents and Chemotherapy, vol. 55, No. 7, pp. 3240-3243 (Jul. 1, 2011).
Extended European Search Report issued by the European Patent Office for European Patent Application No. 14768456.7 dated Aug. 22, 2016 (8 pgs.).
Huttunen, et al., "Obesity and the Risk and Outcome of Infection," International J. of Obesity, vol. 37, No. 3, pp. 333-340 (May 1, 2012).
Kees, et al., "Pharmacokinetics of Moxifloxacin in Plasma and Tissue of Morbidly Obese Patients," J. of Antimicrobial Chemotherapy, vol. 66, No. 10, pp. 2330-2335 (Jul. 5, 2011).
Kingsley, et al., "A Randomized Double-blind, Phase 2 Study to Evaluate Subjective and Objective Outcomes in Patients with Acute Bacterial Skin and Skin Structure Infections Treated with Delafloxacin, Linezolid or Vancomycin, J. of Antimicrobial Chemotherapy," vol. 71, No. 3, pp. 821-829 (Dec. 17, 2015).
No Author, "CAS registry No. 189279-58-1 - Delafloxacin," last retrieved on Jan. 5, 2024 from https://www.sigmaaldrich.com/US/en/product/sigma/sml1869 (2 total pages).
No Author, "CAS registry No. 352458-37-8 - ABT-492 MegluMine," last retrieved Jan. 5, 2024 from https://www.chemicalbook.com/ChemicalProductProperty_EN_CB92666618.htm (3 total pages).
No author, "CAS registry No. 6284-40-8 - N-Methyl-D-glucamine," last retrieved Jan. 5, 2024 from https://commonchemistry.cas.org/detail?cas_rn=6284-40-8&search=6284-40-8 (3 total pages).
No author, "CAS registry No. 869884-78-6 - Radezolid," last retrieved Jan. 5, 2024 from https://commonchemistry.cas.org/detail?cas_rn=869884-78-6&search=869884-78-6 (3 total pages).
Takahata, M., "In Vitro and In Vivo Antimicrobial Activities of T-3811ME, a Novel Des-F(6)- Quinolone," Antimicrobial Agents and Chemotherapy, vol. 43, No. 5, pp. 1077-1084 (May 1999).
U.S. Department of Health and Human Services - Food and Drug Administration, "Draft Guidance for Industry on Acute Bacterial Skin and Skin Structure Infections: Developing Drugs for Treatment; Availability - Docket No. FDA-2010-D-0433," Federal Register, vol. 75, No. 166, 2 total pages (Aug. 27, 2010) - last retrieved Jan. 5, 2024 from https://www.federalregister.gov/documents/2010/08/27/2010-21328/draft-guidance-for-industry- on-acute-bacterial-skin-and-skin-structure-infections-developing-drugs.
Search and Examination Report prepared by Korean Intellectual Property Office and issued by United Arab Emirates Patent Office on Nov. 7, 2023 in United Arab Emirate Patent Application No. P1258/15 (12 total pages).

\* cited by examiner

| BMI ≥ 30 | N | Cure | Failure |
|---|---|---|---|
| Delafloxacin | 33 | 26 (79%) | 7 (21%) |
| Linezolid | 34 | 20 (59%) | 14 (41%) |
| Vancomycin | 41 | 20 (49%) | 21 (51%) |

FIG. 5

| 25< BMI <30 | N | Cure | Failure |
|---|---|---|---|
| Delafloxacin | 28 | 17 (61%) | 11 (39%) |
| Linezolid | 21 | 16 (76%) | 5 (24%) |
| Vancomycin | 24 | 13 (54%) | 11 (46%) |

FIG. 6

| BMI ≤ 25 | N | Cure | Failure |
|---|---|---|---|
| Delafloxacin | 20 | 14 (70%) | 6 (30%) |
| Linezolid | 22 | 14 (64%) | 8 (36%) |
| Vancomycin | 33 | 20 (61%) | 13 (39%) |

FIG. 7

METHODS OF TREATING INFECTIONS IN OVERWEIGHT AND OBESE PATIENTS USING ANTIBIOTICS

CROSS-REFERENCE TO RELATED APPLICATIONS

This application is a National Phase application under 35 U.S.C. § 371 of International Application No. PCT/US2014/027220, filed Mar. 14, 2014, which claims priority to U.S. Provisional Application No. 61/790,179, filed Mar. 15, 2013, the disclosures of which are hereby incorporated by reference in their entireties.

FIELD OF THE INVENTION

The present disclosure relates generally to methods of treating infections in overweight and obese patients using antibiotics.

BACKGROUND

According to statistics compiled by National Health and Nutrition Examination Survey conducted by the National Center for Health Statistics (NCHS) of the U.S. Centers for Disease Control and Prevention (CDC), in 2009-2010, 35.7% of adults in the United States were found to be obese. Ogden, C.L. *NCHS Data Brief* 2012, 82, available at http://www.cdc.gov/nchs/data/databriefs/db82.pdf (last visited Mar. 2, 2013). Overweight and obese individuals are also at increased risk for many diseases and chronic health conditions, including hypertension, osteoarthritis, dyslipidemia, type 2 diabetes, heart disease, stroke, gallbladder disease, sleep apnea and respiratory problems and certain cancers (such as cancers of the pancreas, kidney, prostate, endometrium, breast and colon).

In addition, obesity has been linked to an increased susceptibility to infection through a variety of factors affecting the immune system, rendering these individuals more prone to community-acquired infections, postoperative infections and other nosocomial infections. See Falagas, M. E.; Kompoti, M. *Lancet Infect. Dis.* 2006, 6(7), 438-446. In fact, a disproportionate percentage of patients with serious infections are overweight and obese. A vicious cycle exists for this patient population, as overweight and obese patients are generally less healthy and more likely to acquire an infection, are more likely to suffer complications from the infection which will require hospitalization, where they are then in turn more susceptible to nosocomial infections, or a hospital-acquired infection from other patients, hospital staff, contaminated objects or solutions, or from themselves. The net result is that overweight and obese patients are more likely than non-overweight and obese patients to require treatment with antibiotics.

The determination of dosages of antibiotics in overweight and obese patients can be complicated, as studies have found that pharmacokinetics and pharmacodynamics may be significantly altered in overweight and obese patients. See, e.g., Wurtz, R. et al. *Clin. Infect. Dis.* 1997, 25, 112-118. Several parameters used by physicians in determining dosages for patients (such as volume of distribution ($V_d$), drug clearance (CL), elimination half-life ($t_{1/2}$)) are affected by the patient's weight, and can be particularly difficult to determine in overweight and obese patients. See Hanley, M. J. et al. *Clin. Pharmacokinetics* 2010, 49(2), 71-87. For example, renal function and some hepatic function are increased in overweight and obese patients, which can complicate the calculation of factors used to determine dosing for antibiotics. See, e.g., Griffin, K. A. et al. *Am. J. Physiol. Renal. Physiol.* 2008, 294(4), F685-F696. Methods of calculating renal function (e.g., glomerular filtration rate (GFR) or creatinine clearance rate) for the purpose of determining a dosage regimen often include a variable for the patient's weight. One of the most common methods used to adjust doses of drugs which are excreted renally, such as certain antibiotics, is the Cockcroft-Gault formula, which calculates an estimate creatinine clearance rate. However, this formula depends on Total Body Weight, which is problematic because GFR has been found to increase as a patient's weight increases, making the Cockcroft-Gault formula less reliable for overweight and obese patients. See Chagnac A. et al. *Am. J. Physiol. Renal. Physiol.* 2000, 278, F817-F822; Pai, M. P. et al. *Antimicrobial Agents Chemother.* 2007, 51(8), 2741-2747. Further complicating matters is that various other weight measurements are available, such as Body Mass Index (BMI), Body Surface Area, Ideal Body Weight (IBW), Fat-Free Weight, Lean Body Weight, Adjusted Body Weight, Percent IBW and Predicted Normal Weight. While calculation methods for renal clearance of estimated GFR (eGFR) using one or more versions of the Modification of Diet in Renal Disease formula do not adjust for body mass, it is well known that this method underestimates eGFR for overweight and obese patients and overestimates eGFR for underweight patients, and is of questionably utility for these patients.

Because known methods of antibiotic dosing rely, at least in part, on the patient's weight, dosages provided to overweight and obese patients are greater than those provided to non-overweight and obese patients. Because of this larger total dose, overweight and obese patients are more likely to experience toxicities and side effects of antibiotic drugs, such as allergies, rashes, hives, anaphylaxis, hypersensitivities, pruritus, infusion site pain, fatigue, gastrointestinal disorder, thrombocytopenia, phototoxicity, elevated liver enzymes, dysglycemia, QT prolongation, diarrhea, abdominal pain, nausea, vomiting, drug fever, serum sickness, vaginal candidiasis, renal toxicity, ototoxicity, dizziness, nystagmus, headache, liver toxicity, anorexia, hemolytic anemia, peripheral neuropathy, flushing, hypotension, itching, phlebitis, taste alteration, photosensitivity, tooth discoloration, lethargy, pseudomembranous colitis, jaundice and metallic taste. See Susan London "Televancin Adds Option for Obese Patients with SSSIs" Internal Medicine News Oct. 18, 2011, available at http://www.internalmedicinenews-.com/news/more-top-news/single-view/telavancin-adds-option-for-obese-patients-with-sssis/8eedc843f6.html (last visited Mar. 2, 2013). These toxicities and side effects can lead to treatment failure. Because of this increased risk for overweight and obese patients receiving antibiotics, these individuals must often be monitored for side effects and toxicities such as renal and liver toxicity, resulting in higher total treatment costs and/or lower efficacy. This can be taxing on physicians and clinicians, and can require extended hospital stays, further exposing the patient to additional nosocomial infections. Thus, there remains a need for improved methods for treating bacterial infections in overweight and obese patients comprising administering a therapeutically effective amount of an antibiotic compound that is based upon the patient's BMI.

BRIEF DESCRIPTION OF THE DRAWINGS

FIG. 5 shows a comparison of the cure/failure rates in patients treated for ABSSSI with either delafloxacin, linezolid or vancomycin for patients having a BMI greater than or equal to 30 (obese, severely obese, morbidly obese and super obese).

FIG. 6 shows a comparison of the cure/failure rates in patients treated for ABSSSI with either delafloxacin, linezolid or vancomycin for patients having a BMI greater than 25 and less than 30 (overweight).

FIG. 7 shows a comparison of the cure/failure rates in patients treated for ABSSSI with either delafloxacin, linezolid or vancomycin for patients having a BMI less than or equal to 25 (normal).

SUMMARY

Figure 1:
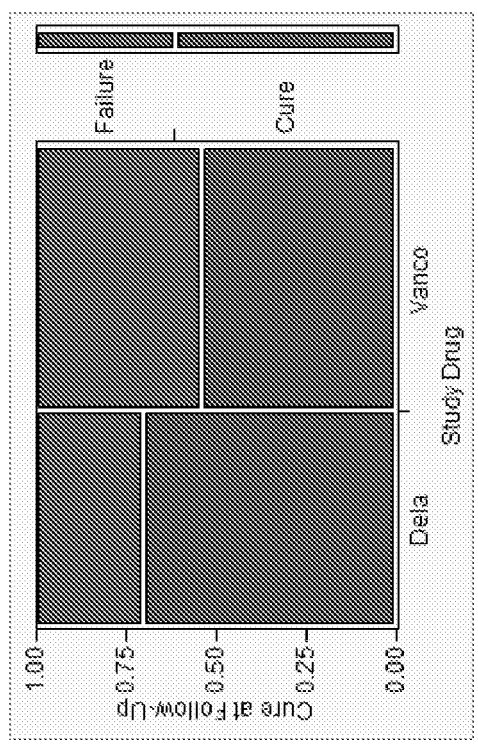
FIG. 1 shows a comparison of cure and failure rates in patients treated for Acute Bacterial Skin and Skin Structure Infections (ABSSSI) with either delafloxacin or vancomycin for all patients (i.e. having any BMI).

The present disclosure relates generally to methods of treating infections in overweight and obese patients using antibiotics.

In one aspect, a method of treating a bacterial infection in an overweight or obese patient is disclosed, the method comprising administering a therapeutically effective amount of an antibiotic compound to an overweight or obese patient in need thereof, wherein the therapeutically effective amount is not based on the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is independent of the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not determined by the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not calculated from the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not based on the weight or body surface area of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is less than the amount that would be administered to the patient on a basis of about 10 mg/kg.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is from about 0.01 mg/kg to about 7 mg/kg.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is from about 10 mg/day to about 600 mg/day.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is about 1.5 to about 10-fold lower than a dose of the antibiotic compound that produces at least one side effect selected from the group consisting of allergies, rashes, hives, anaphylaxis, hypersensitivities, pruritus, infusion site pain, fatigue, gastrointestinal disorder, thrombocytopenia, phototoxicity, elevated liver enzymes, dysglycemia, QT prolongation, diarrhea, abdominal pain, nausea, vomiting, drug fever, serum sickness, vaginal candidiasis, renal toxicity, ototoxicity, dizziness, nystagmus, headache, liver toxicity, anorexia, hemolytic anemia, peripheral neuropathy, flushing, hypotension, itching, phlebitis, taste alteration, photosensitivity, tooth discoloration, lethargy, pseudomembranous colitis, jaundice and metallic taste.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is based on the therapeutically effective amount for a patient who is not overweight or obese.

DETAILED DESCRIPTION

Unless otherwise defined, all technical and scientific terms used herein have the same meaning as commonly understood by one of ordinary skill in the art to which this disclosure belongs. In the case of conflict, the present specification will control. Although methods and materials similar or equivalent to those described herein can be used in accordance with the present disclosure, suitable methods and materials are described below. All publications, patent applications, patents, and other references mentioned herein are incorporated by reference in their entirety. In the specification, the singular forms also include the plural, unless the context clearly dictates otherwise. In case of conflict, the present specification, including definitions, will control. In addition, the materials, methods, and examples are illustrative only and not intended to be limiting. Other features and advantages of the present disclosure will be apparent from the following detailed description, and from the claims.

The present disclosure results in part from the discovery that overweight and obese patients with infections were not being properly dosed with antibiotics, resulting in high incidence of adverse events and reduced efficacy. The inventors have surprisingly found that bacterial infections can be treated in overweight and obese patients without the need to adjust the dosage of antibiotics for the patient's weight.

For example, in one particular Phase 2b clinical trial of delafloxacin for the treatment of Acute Bacterial Skin and Skin Structure Infections (ABSSSI), including methicillin-resistant *Staphylococcus aureus* (MRaSA), the inventors have discovered that when delafloxacin was administered at a flat dosage of 300 mg BID to patients regardless of weight, cure rates were superior to those rates achieved with administration of a flat dosage of linezolid (600 mg BID) and vancomycin (1,000-2,000 mg BID), with no increase in adverse events. While the trial was not designed to demonstrate statistical significance, for the primary endpoint of Investigators' Global Assessment of Cure, delafloxacin demonstrated a statistically significant efficacy advantage as compared to vancomycin, including in obese patients (95% Confidence Interval −30.3%, −2.3%, p=0.031). Additionally, delafloxacin demonstrated numerical benefit over both linezolid and vancomycin in the secondary endpoint, cessation of lesion spread and absence or resolution of fever at 48 to 72 hours, with cure rates of approximately 78%, 75%, and 73%, respectively. Furthermore, delafloxacin showed that a greater percentage of patients experience a 30% or greater reduction in the size of the lesion at 48 to 72 hours than either comparator. The inventors have surprisingly discovered from the data generated in this Phase 2b study that the clinical activity of delafloxacin is maintained with increased patient weight, while the clinical activity of linezolid and vancomycin decline as typically seen in the overweight and obese population. Relative differences in efficacy become more pronounced as weight increases. Delafloxacin also demonstrates a greater ratio of potency and local levels per organism minimum inhibitor concentration for typical ABSSSI bacteria. Further, delafloxacin has no specific limiting toxicity as do vancomycin (kidney) and linezolid (bone marrow).

The methods disclosed herein for treating infections in overweight and obese patients provide numerous advantages over the methods known in the art. For example, with traditional methods, as dosages increase with the weight of an overweight and obese patient, the potential for toxicity and adverse events also increases. In contrast, the present methods provide for consistently lower doses of antibiotics which reduce the toxicity and adverse event risks seen in prior methods. Further, because of the increased potential for toxicity and adverse events brought by prior methods, patients frequently require close monitoring. In contrast, the need to monitor overweight and obese patients treated with the present methods is significantly reduced. This also results in the possibility for outpatient administration or earlier release of patients, with later follow-up, reducing burdens on patients and health care providers. Compliance can also be expected to be improved because of the reduction in side effects. Still further, the present methods reduce the burden on physicians and clinicians to calculate dosages for patients based on complex calculations of renal function, volume of distribution and other relevant factors. Instead, a consistent low dosage may be used without reference to the patient's weight. Still further, because overweight and obese patients are generally less healthy than non-overweight and obese patients, overweight and obese patients tend to be taking other medications, such as for hypertension, diabetes, etc. With the reduced dosage of antibiotics used in the present methods comes a reduced potential for drug-drug interactions with an overweight and obese patient's other medications.

A. Definitions

The content of any publication cited herein is incorporated by reference.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the method remains operable. Moreover, two or more steps or actions can be conducted simultaneously.

The term "obese" as used herein refers to a Body Mass Index (BMI) greater than or equal to 30 and less than 35. "Obese" includes the terms "obese," "severely obese," "morbidly obese" and "super obese."

The term "normal" as used herein with respect to body weight refers to a BMI less than or equal to 25.

The term "overweight" as used herein refers to a BMI greater than 25 and less than 30.

The term "severely obese" as used herein refers to a BMI greater than or equal to 35 and less than 40.

The term "morbidly obese" as used herein refers to a BMI greater than or equal to 40 and less than 45.

The term "super obese" as used herein refers to a BMI greater than or equal to 45.

The term "Body Mass Index" (BMI) is defined as a measure of body fat based on height and weight that applies to adult men and women. It is calculated as either a patient's mass in kilograms divided by the square of their height in meters, or 703 times a patient's mass in pounds divided by the square of their height in inches. These definitions are displayed formulaically below:

$$BMI = mass\ (kg)/(height\ (m))^2$$

$$BMI = (mass\ (lb)/(height\ (in))^2) \times 703$$

The term "therapeutically effective amount" as used herein refers to the quantity of a compound which, when administered to a patient, results in a discernible physiological effect in the patient.

The term "cure" or "Investigators' Global Assessment of Cure" as used herein refers to complete resolution of all signs and symptoms at the follow-up visit.

The term "failure" as used herein refers to anything other than complete resolution of all signs and symptoms at the follow-up visit.

One or more disclosed compounds, can be incorporated into a pharmaceutical composition or medicament. The disclosed compounds can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The pharmaceutical composition or medicament can also contain a pharmaceutically acceptable vehicle, diluent, excipient or carrier and optional adjuvants, flavorings, colorants, wetting agents, emulsifying agents, pH buffering agents and preservatives. Some suitable pharmaceutically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the patient being treated.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "side effect," "adverse event" and "adverse effect" are used interchangeably herein and refer to the occurrence of an undesired physiological effect in a patient.

The term "patient" as used herein refers to a human to be treated by the presently disclosed methods.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The pharmaceutically acceptable salts disclosed herein can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In one embodiment, non-aqueous media, for example ether, ethyl acetate, ethanol, isopropanol, or acetonitrile are useful for forming salts of the present compounds. Lists of suitable salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present disclosure.

Additionally, the compounds disclosed herein, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable esters" refer to derivatives of the disclosed compounds wherein the parent compound is modified by an alcohol ester of a carboxylic acid or a carboxylic acid ester of an alcohol. The compounds disclosed herein can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

As used herein, the term "unit dosage", means a single dose of a pharmaceutical composition that is intended to be administered in its entirety. A unit dosage is a convenient form for administering a premeasured amount of a drug active.

In some embodiments, the compositions of the present disclosure comprise a quinolone carboxylic acid compound, or a pharmaceutically acceptable salt, ester, or prodrug thereof, as an antimicrobial compound. The quinolone carboxylic acid compound is alternatively known as a pyridone carboxylic acid or a pyridone carboxylic acid derivative. As used herein the term "quinolone carboxylic acid compounds" includes quinolone carboxylic acid compounds, useful herein which are described, including their synthesis, formulation, and use, in U.S. Pat. No. 6,156,903, to Yazaki et al., issued Dec. 5, 2000 and its certificates of correction of Nov. 13, 2001 and Dec. 11, 2001; U.S. Pat. No. 6,133,284, to Yazaki et al., issued Oct. 17, 2000; U.S. Pat. No. 5,998, 436, to Yazaki et al., issued Dec. 7, 1999 and its certificates of correction of Jan. 23, 2001, Oct. 30, 2001, and Dec. 17, 2002; PCT Application No. WO 2006/110815, to Abbott Laboratories, published Oct. 19, 2006; PCT Application No. WO 2006/042034, to Abbott Laboratories, published Apr. 20, 2006, PCT Application No. WO 2006/015194, to Abbott Laboratories, published Feb. 9, 2006; PCT Application No. WO 01/34595, to Wakunaga Pharmaceutical Co., Ltd., published May 17, 2001; and PCT Application No. WO 97/11068, to Wakunaga Pharmaceutical Co., Ltd., published Mar. 27, 1997; the foregoing all of which are incorporated by reference herein in their entirety.

In some embodiments, quinolone carboxylic acid compounds disclosed herein include compounds corresponding to the following structure:

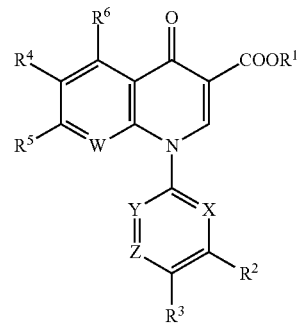

wherein R¹ represents a hydrogen atom or a carboxyl protective group; R² represents a hydroxyl group, a lower alkoxy group, or a substituted or unsubstituted amino group; R³ represents a hydrogen atom or a halogen atom; R⁴ represents a hydrogen atom or a halogen atom; R⁵ represents a halogen atom or an optionally substituted saturated cyclic amino group; R⁶ represents a hydrogen atom, a halogen atom, a nitro group, or an optionally protected amino group; X, Y and Z may be the same or different and respectively represent a nitrogen atom, —CH═ or —CR⁷═ (wherein R⁷ represents a lower alkyl group, a halogen atom, or a cyano group); and W represents a nitrogen atom or —CR⁸═ (wherein R⁸ represents a hydrogen atom, a halogen atom, or a lower alkyl group), or a pharmaceutically acceptable salt or ester thereof.

In some embodiments, at least one of X, Y and Z represent a nitrogen atom.

In some embodiments, R¹, R², R³, R⁴, R⁵, R⁶, R⁷, R⁸, W, X, Y, and Z are defined for Formula 2, and not as defined for the cyclodextrins.

In some embodiments, when R¹ represents a hydrogen atom, R² represents an amino group, R³ and R⁴ represent a fluorine atom, R⁶ represents a hydrogen atom, X represents a nitrogen atom, Y represents —CR⁷═ (wherein R⁷ represents a fluorine atom), Z represents —CH═, and W is —CR⁸═ (wherein R⁸ represents a chlorine atom), then R⁵ is not a 3-hydroxyazetidine-1-yl group.

In other embodiments, the compositions disclosed herein comprise a quinolone carboxylic acid derivative corresponding to the following compound (A),

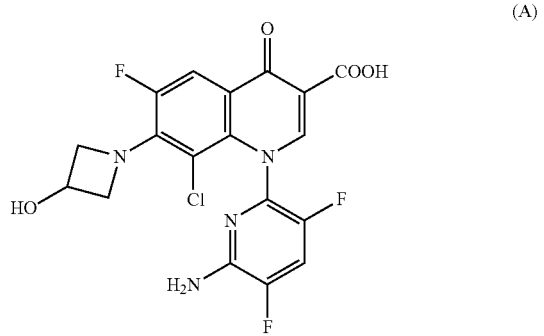 [SMILES: Nc1nc(-n2cc(C(=O)O)c(=O)c3cc(F)c(N4CC(O)C4)c(Cl)c32)c(F)cc1F]

(A)

or a pharmaceutically acceptable salt or ester thereof. In other embodiments, the compositions disclosed herein comprise the quinolone carboxylic acid derivative D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate. In other embodiments, the compositions disclosed herein comprise a crystalline form of the quinolone carboxylic acid D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate In other embodiments, the compositions disclosed herein comprise a the quinolone carboxylic acid D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate. In other embodiments, the compositions disclosed herein comprise a crystalline form of the quinolone carboxylic acid D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate.

In some embodiments, the compositions disclosed herein comprise from about 100 mg to about 500 mg of delafloxacin meglumine. In other embodiments, the compositions disclosed herein comprise about 300 mg of delafloxacin meglumine.

B. Embodiments

The present disclosure relates generally to methods of treating infections in overweight and obese patients using antibiotics.

In one aspect, a method of treating a bacterial infection in an overweight or obese patient is disclosed, the method comprising administering a therapeutically effective amount of an antibiotic compound to an overweight or obese patient in need thereof, wherein the therapeutically effective amount is not based on the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is independent of the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not determined by the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not calculated from the body mass index of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is not based on the weight or body surface area of the patient.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is less than the amount that would be administered to the patient on a basis of about 10 mg/kg.

In some embodiments, the therapeutically effective amount is less than the amount that would be administered to the patient on a basis of about 9 mg/kg. In some embodiments, the therapeutically effective amount is less than the amount that would be administered to the patient on a basis of about 8 mg/kg. In some embodiments, the therapeutically effective amount is less than the amount that would be administered to the patient on a basis of about 7 mg/kg. In some embodiments, the therapeutically effective amount is less than the amount that would be administered to the patient on a basis of about 6 mg/kg. In some embodiments, the therapeutically effective amount is less than the amount that would be administered to the patient on a basis of about 5 mg/kg. In some embodiments, the therapeutically effective amount is less than the amount that would be administered to the patient on a basis of about 4 mg/kg. In some embodiments, the therapeutically effective amount is less than the amount that would be administered to the patient on a basis of about 3 mg/kg. In some embodiments, the therapeutically effective amount is less than the amount that would be administered to the patient on a basis of about 2 mg/kg. In some embodiments, the therapeutically effective amount is less than the amount that would be administered to the patient on a basis of about 1 mg/kg. In some embodiments, the therapeutically effective amount is less than the amount that would be administered to the patient on a basis of about 0.75 mg/kg. In some embodiments, the therapeutically effective amount is less than the amount that would be administered to the patient on a basis of about 0.5 mg/kg. In some embodiments, the therapeutically effective amount is less than the amount that would be administered to the patient on a basis of about 0.25 mg/kg. In some embodiments, the therapeutically effective amount is less than the amount that would be administered to the patient on a basis of about 0.1 mg/kg. In some embodiments, the therapeutically effective amount is less than the amount that would be administered to the patient on a basis of about 0.05 mg/kg.

In some embodiments, the therapeutically effective amount of the antibiotic compound is administered on a mg/kg once daily basis. In other embodiments, the therapeutically effective amount of the antibiotic compound is administered on a mg/kg twice daily basis.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is from about 0.01 mg/kg to about 7 mg/kg.

In some embodiments, the therapeutically effective amount is from about 0.1 mg/kg to about 5 mg/kg. In some embodiments, the therapeutically effective amount is from about 0.5 mg/kg to about 3 mg/kg. In some embodiments, the therapeutically effective amount is from about 1 mg/kg to about 2 mg/kg.

In some embodiments, the therapeutically effective amount of the antibiotic compound is administered on a mg/kg once daily basis. In some embodiments, the therapeutically effective amount of the antibiotic compound is administered on a mg/kg twice daily basis.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is from about 10 mg/day to about 600 mg/day.

In some embodiments, the therapeutically effective amount is from about 50 mg/day to about 500 mg/day. In some embodiments, the therapeutically effective amount is from about 100 mg/day to about 400 mg/day. In some embodiments, the therapeutically effective amount is from about 200 mg/day to about 300 mg/day.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is about 1.5 to about 10-fold lower than a dose of the antibiotic compound that produces at least one side effect selected from the group consisting of allergies, rashes, hives, anaphylaxis, hypersensitivities, pruritus, infusion site pain, fatigue, gastrointestinal disorder, thrombocytopenia, phototoxicity, elevated liver enzymes, dysglycemia, QT prolongation, diarrhea, abdominal pain, nausea, vomiting, drug fever, serum sickness, vaginal candidiasis, renal toxicity, ototoxicity, dizziness, nystagmus, headache, liver toxicity, anorexia, hemolytic anemia, peripheral neuropathy, flushing, hypotension, itching, phlebitis, taste alteration, photosensitivity, tooth discoloration, lethargy, pseudomembranous colitis, jaundice and metallic taste.

In some embodiments, the therapeutically effective amount is about 2- to about 8-fold lower. In some embodiments, the therapeutically effective amount is about 3- to about 6-fold lower. In some embodiments, the therapeutically effective amount is about 4- to about 5-fold lower.

In another aspect, a method of treating a bacterial infection in an overweight or obese patient is disclosed, the method comprising administering a therapeutically effective amount of an antibiotic compound to an overweight or obese patient in need thereof, wherein the therapeutically effective amount is based on the therapeutically effective amount for a patient who is not overweight or obese.

In some embodiments, the antibiotic compound is selected from the group consisting of amikacin, gentamicin, kanamycin, neomycin, netilmicin, tobramycin, paromomycin, spectinomycin, geldanamycin, herbimycin, rifaximin, loracarbef, ertapenem, doripenem, imipenem, cilastatin, meropenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, linomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin, penicillin G, penicillin V, piperacillin, temocillin, ticarcillin, clavulanate, sulbactam, tazobactam, bacitracin, colistin, polymyxin B, ciprofloxacin, delafloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilamide, sulfasalazine, sulfisoxazole, trimethoprim, sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifampin, rifabutin, rifapentine, streptomycin, arsphenamine, chloramphenicol, fosfomycin, fusidic acid, metronidazole, mupirocin, platensimvcin, quinupristin, dalfopristin, thiamphenicol, tigecycline, tinidazole, trimethoprim or combinations thereof.

In some embodiments, the antibiotic compound is a quinolone carboxylic acid antibiotic. In some embodiments, the compound is delafloxacin.

In some embodiments, the dosage is between about 10 mg/day and about 600 mg/day. In some embodiments, the therapeutically effective amount is between about 50 mg/day to about 500 mg/day. In some embodiments, the therapeutically effective amount is between about 100 mg/day to about 400 mg/day. In some embodiments, the therapeutically effective amount is between about 200 mg/day to about 300 mg/day.

In some embodiments, the overweight or obese patient has a body mass index greater than or equal to 25. In some embodiments, the overweight or obese patient has a body mass index greater than or equal to 30. In some embodiments, the overweight or obese patient has a body mass index greater than or equal to 35. In some embodiments, the overweight or obese patient has a body mass index greater than or equal to 40.

Phase 2b Clinical Trial

A Phase 2b clinical trial was designed to compare the efficacy of delafloxacin for the treatment of ABSSSI (including infections caused by MRSA) to Zyvox (linezolid), with and without aztreonam, and vancomycin, with and without aztreonam.

Delafloxacin met primary and secondary efficacy endpoints evaluated through end of 2011, including endpoints based on the draft guidance from the FDA in ABSSSI. Of note, although this Phase 2b trial was not designed to demonstrate statistical significance, for the primary endpoint of Investigators' Global Assessment of Cure, delafloxacin demonstrated a statistically significant efficacy advantage as compared to vancomycin (95% Confidence Interval −30.3%, −2.3%; p=0.031). Additionally, delafloxacin demonstrated numerical benefit over both Zyvox and vancomycin in the secondary endpoint, cessation of lesion spread and absence or resolution of fever at 48 to 72 hours, with cure rates of approximately 78%, 75%, and 73%, respectively.

Furthermore, delafloxacin showed that a greater percentage of patients experience a 30% or greater reduction in the size of the lesion at 48 to 72 hours than either comparator.

Phase 2b ABSSSI Results
Delafloxacin (300 mg BID) versus Zyvox (600 mg BID)
and vancomycin (1,000 to 2,000 mg BID)

|  | Delafloxacin | Zyvox (with and without Aztreonam) | Vancomycin (with and without Aztreonam) |
|---|---|---|---|
| Investigators' Global Assessment of Cure[1] | | | |
| Response Rate | 57/81 | 50/77 | 53/98 |
| Percent Clinical Cure (ITT[2]) | 70.4% | 64.9% | 54.1% |
| Investigators' Global Assessment of Cure in Patients with Confirmed MRSA | | | |
| Response Rate | 19/29 | 21/34 | 21/32 |
| Percent Clinical Cure (MITT[1]) | 65.5% | 61.8% | 65.6% |
| Objective Endpoint at 48 to 72 hours[1] | | | |
| Response Rate | 61/78 | 56/75 | 69/95 |
| Percent Cessation of Spread of Erythema and Absence of Fever at 48 to 72 Hours | 78.2% | 74.7% | 72.6% |

[1] The differential between the cure rates of delafloxacin and vancomycin is statistically significant (95% Confidence Interval −30.3%, −2.3%; p = 0.031).
[2] ITT—Intent-to-Treat
[1] MITT—Microbiological Intent-to-Treat
[1] Objective efficacy measure proposed by FDA in Draft Guidance for Drug Development in ABSSS1 in 2010.

Overall adverse event rates were statistically equivalent across the study for delafloxacin (74%), Zyvox (72%) and vancomycin (65%). The leading adverse event associated with delafloxacin was gastrointestinal, or GI, disorder with mild to moderate diarrhea as the most common specific event. The other common adverse events in this trial were nausea, vomiting, fatigue, headache, dizziness and infusion site pain. The leading adverse event for Zyvox was also GI disorder, with the most common specific event being nausea. The leading adverse event for vancomycin was disorders of the skin, with the most common specific event being pruritus, or itching. In the Zyvox arm, two subjects experienced thrombocytopenia. In the vancomycin arm, three patients experienced renal issues, including two renal failures. Importantly, as observed in earlier Phase 2 studies, delafloxacin did not demonstrate evidence for the toxicities that have been common in the fluoroquinolone class of antibiotics, such as phototoxicity, elevated liver enzymes, dysglycemia and QT prolongation.

The design of this trial grew out of extensive discussion with FDA about new clinical trial endpoints following an End-Of-Phase 2 meeting in April 2010, and subsequent discussions during the FDA's review of the trial protocol. Prior to the Phase 2b clinical trial, a Phase 2a clinical trial had been conducted, the results of which supported our decision to design and conduct a Phase 2b clinical trial. The Phase 2b study was a randomized, double-blind comparison of delafloxacin, Zyvox, with and without aztreonam, and vancomycin, with and without aztreonam, using objective efficacy measures to evaluate the relative clinical responses in subjects with ABSSSI; aztreonam was added by the investigator based on the believed or confirmed presence of Gram-negative bacteria. The trial enrolled a total of 256 subjects across 34 centers in the United States. Subjects were randomized into three treatment arms to receive either delafloxacin, 300 mg intravenously every 12 hours, or the recommended dosing for Zyvox (600 mg every 12 hours), both with and without aztreonam, or vancomycin (1,000 to 2,000 mg every 12 hours), both with and without aztreonam. The primary endpoint for the study was the Investigators' Global Assessment of Cure. Additionally, a key goal was to assess the utility, variability and measurement techniques of several objective measures of clinical efficacy for use in future clinical trials. Efficacy was evaluated at multiple time points during the study, with a focus on the first five days of administration, through assessments of objective signs and symptoms of infection such as the extent/size of infection, fever, measurement of biochemical markers of inflammation and culture and susceptibility testing of bacterial isolates. Delafloxacin also demonstrated numerical benefit over both Zyvox and vancomycin in the microbiological intent-to-treat population, a subset of the intent-to-treat population, with respect to the Investigators' Global Assessment of Cure and the cessation of lesion spread and absence of fever at 48 and 72 hours. The types of infections treated included abscess, wound, cellulitis and burn related infections.

C. Detailed Description of the Figures

The following detailed description of the figures describes the results of the Phase 2b clinical trial discussed herein.

FIG. 1 shows cure/failure rates for treatment of ABSSSI with delafloxacin and vancomycin in all patients (i.e. having any BMI). The p-value for this data is 0.0310, with n=81 for delafloxacin and n=98 for vancomycin.

Figure 2:
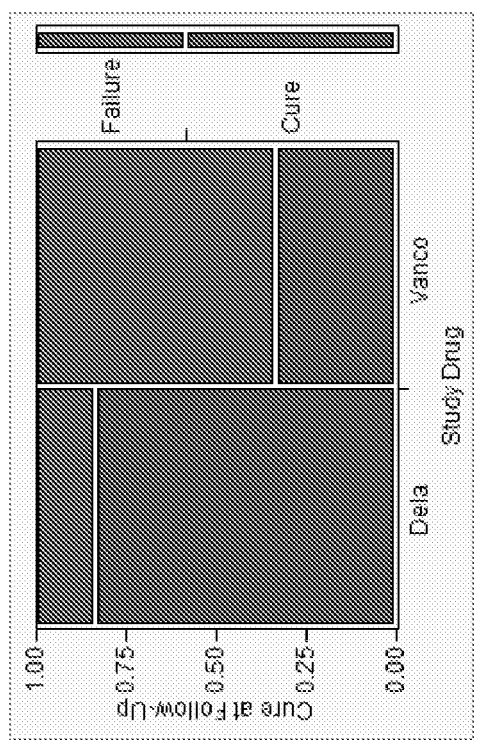
FIG. 2 shows a comparison of cure and failure rates in patients treated for ABSSSI with either delafloxacin or vancomycin for patients having a BMI greater than or equal to 40 (morbidly obese and super obese).

FIG. 2 shows cure/failure rates for treatment of ABSSSI with delafloxacin and vancomycin in patients having a BMI greater than or equal to 40 (super obese and morbidly obese). The p-value for this data is 0.2424, with n=6 for delafloxacin and n=6 for vancomycin.

Figure 3:
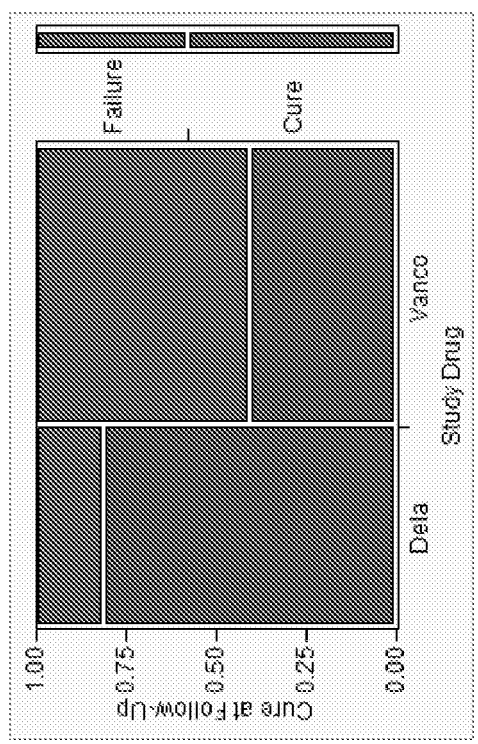
FIG. 3 shows a comparison of cure and failure rates in patients treated for ABSSSI with either delafloxacin or vancomycin for patients having a BMI greater than or equal to 35 (severely obese, morbidly obese and super obese).

FIG. 3 shows cure/failure rates for treatment of ABSSSI with delafloxacin and vancomycin in patients having a BMI greater than or equal to 35 (severely obese, morbidly obese and super obese). The p-value for this data is 0.0202, with n=16 for delafloxacin and n=22 for vancomycin.

Figure 4:
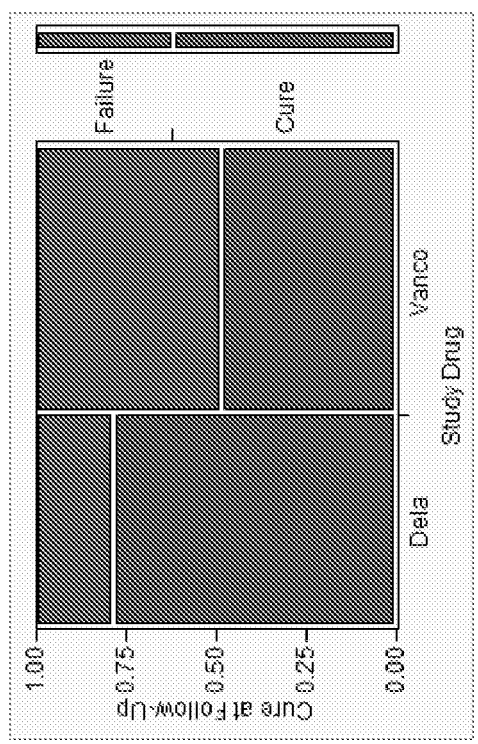
FIG. 4 shows a comparison of cure and failure rates in patients treated for ABSSSI with either delafloxacin or vancomycin for patients having a BMI greater than or equal to 30 (obese, severely obese, morbidly obese and super obese).

FIG. 4 shows cure/failure rates for treatment of ABSSSI with delafloxacin and vancomycin in patients having a BMI greater than or equal to 30 (obese, severely obese, morbidly obese and super obese). The p-value for this data is 0.0093, with n=33 for delafloxacin and n=41 for vancomycin.

FIG. 5 shows a comparison of the cure/failure rates in patients treated for ABSSSI with either delafloxacin, linezolid or vancomycin for patients having a BMI greater than or equal to 30 (obese, severely obese, morbidly obese and super obese).

FIG. 6 shows a comparison of the cure/failure rates in patients treated for ABSSSI with either delafloxacin, linezolid or vancomycin for patients having a BMI greater than 25 and less than 30 (overweight).

FIG. 7 shows a comparison of the cure/failure rates in patients treated for ABSSSI with either delafloxacin, linezolid or vancomycin for patients having a BMI less than or equal to 25 (normal).

Antibiotics

A wide range of antimicrobial agents can be used in the methods disclosed herein. These antimicrobial agents can provide their therapeutic effect by a variety of biochemical or biophysical mechanisms. Such agents useful in the present disclosure can include those which bind to or modulate ribosomal RNA, for example bacterial ribosomal RNA. Such agents also useful in the present disclosure can include those which bind to or modulate the large ribosomal subunit, for example the large ribosomal subunit of a bacterial organism. Such agents also useful in the present disclosure can include those which bind to or modulate DNA topoisomerases, for example bacterial DNA topoisomerases. Such agents also useful in the present disclosure can include those which bind to or modulate bacterial DNA gyrase, for example bacterial DNA gyrase, i.e. gyrase being an example of a topoisomerase. Such agents also useful in the present disclosure can include those which bind to or modulate bacterial topoisomerase IV.

Useful antimicrobial agents include antibacterial agents, antifungal agents, anti-viral agents, and anti-parasitic agents. Useful chemical classes of compounds include those selected from oxazolidinones (e.g., linezolid, torezolid, tedizolid, eperezolid, N-[3-(2-fluoro-4'-{[(3H-[1,2,3]triazol-4-ylmethyl)-amino]-methyl}-biphenyl-4-yl)-2-oxo-oxazolidin-5-(S)-ylmethyl]-acetamide, and other oxazolidinones), macrolides, ketolides, streptogramin As, streptogramin Bs, chloramphenicol and chloramphenicol derivatives, fluorfenicol and fluorfenicol derivatives, glycopeptides, pleuromutilins, aminoglycosides, beta-lactams and carbapenems (including carbapenems with a 7-acylated imidazo[5-1,b]thiazole-2-yl group directly attached to the carbapenem moiety of the C-2 position), cephalosporins, lincosamides, quinolones and fluoroquinolones (e.g., pyridonecarboxylic acid derivatives, garenoxacin, gatifloxacin, gemifloxacin, levofloxacin, moxifloxacin, etc.), benzoheterocyclic compounds, aminomethylcycline compounds, dalbavancin, daptomycin, oritavancin, televancin, and mixtures thereof. It should be noted that compounds useful herein can in some instances be classified in more than one way. The description or classification of a compound or compounds is not intended to limit that compound or compounds, but is being done for the sake of convenience.

The compounds useful in the present disclosure can include the pharmaceutically acceptable salts, esters, or prodrugs thereof. The disclosure further provides methods for synthesizing any one of the compounds of the present disclosure. The disclosure also provides pharmaceutical compositions comprising an effective amount of one or more of the compounds of the present disclosure and a pharmaceutically acceptable carrier. The present disclosure further provides methods for making these compounds, carriers, and pharmaceutical compositions.

Oxazolidinones

Oxazolidinones and their pharmaceutically acceptable salts, esters, and prodrugs thereof, can be used in the methods, compositions, and uses of the present disclosure. Linezolid, i.e. (N-[[(5S)-3-[3-fluoro-4-(4-morpholinyl)phenyl]-2-oxo-5-oxazolidinyl]methyl]acetamide), which is sold under the trade name or proprietary name Zyvox, is a commercially marketed oxazolidinone. See U.S. Pat. No. 6,559,305 B1, to Bergren, issued May 6, 2003; U.S. Pat. No. 5,688,792, to Barbachyn et al., issued Nov. 18, 1997; and M. R. Barbychan et al., "Development of Linezolid: Oxazolidinone Structure-Activity Relationships Leading to Linezolid", Angew. Chem. Int. Ed., 42, pp. 2010-2023 (2003). Other oxazolidinones and other compounds useful in the methods, compositions, and uses of the present disclosure are described in U.S. Pat. No. 6,969,726 B2, to Lou et al., issued Nov. 29, 2005; PCT Application No. WO 2006/022794, to Rib-X Pharmaceuticals, Inc., published Mar. 2, 2006; PCT Application No. WO 2005/070904, to Rib-X Pharmaceuticals, Inc., published Aug. 4, 2005; PCT Application No. WO 2005/061468, to Rib-X Pharmaceuticals, Inc., published Jul. 7, 2005; PCT Application No. WO 2005/019211, to Rib-X Pharmaceuticals, Inc., published Mar. 3, 2005; PCT Application No. WO 2005/012271, to Rib-X Pharmaceuticals, Inc., published Feb. 10, 2005; PCT Application No. WO 2005/012270, to Rib-X Pharmaceuticals, Inc., published Feb. 10, 2005; U.S. Patent Application Publication No. US 2005/0043317 A1, to Zhou et al., published Feb. 24, 2005; U.S. Patent Application Publication No. US 2005/0153971 A1, to Chen et al., published Jul. 14, 2005; U.S. Pat. No. 5,654,435 to Barbachyn et al., issued Aug. 5, 1997 and, PCT Application No. WO 2001/094342, to Dong A Pharm. Co., Ltd., published Dec. 13, 2001, and PCT Application No., WO 01/081350, to AstraZeneca AB and AstraZeneca UK Limited, published Nov. 1, 2001.

Nonlimiting examples of oxazolidinones include those selected from the group consisting of the following compounds

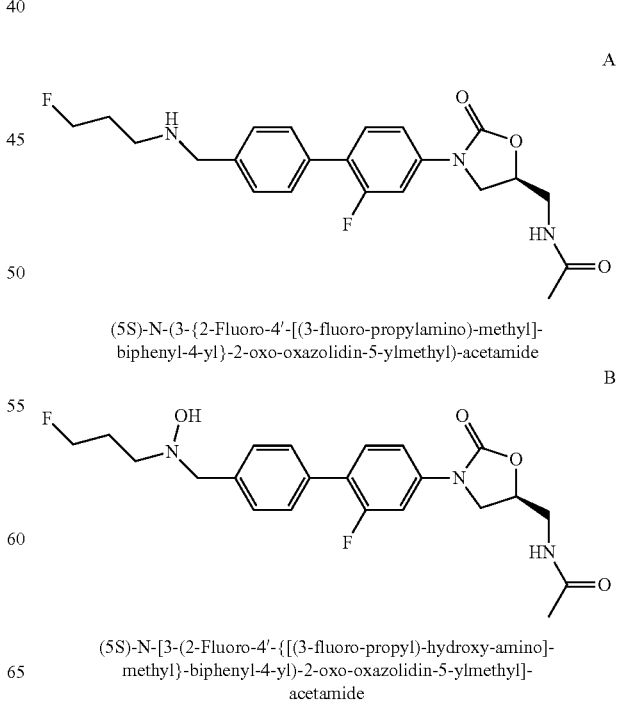

A (5S)-N-(3-{2-Fluoro-4'-[(3-fluoro-propylamino)-methyl]-biphenyl-4-yl}-2-oxo-oxazolidin-5-ylmethyl)-acetamide

B (5S)-N-[3-(2-Fluoro-4'-{[(3-fluoro-propyl)-hydroxy-amino]-methyl}-biphenyl-4-yl)-2-oxo-oxazolidin-5-ylmethyl]-acetamide

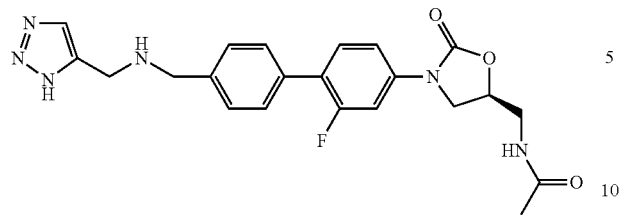

N-[3-(2-Fluoro-4′-{[(3H-[1,2,3]triazol-4-ylmethyl)-amino]-
methyl}-biphenyl-4-yl)-2-oxo-oxazolidin-5-(S)-ylmethyl]-
acetamide

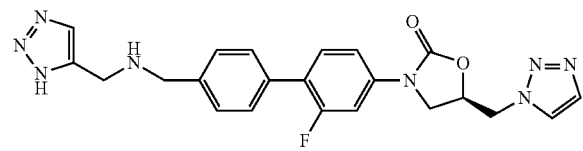

3-(2-Fluoro-4′-{[(3H-[1,2,3]triazol-4-ylmethyl)-amino]-
methyl}-biphenyl-4-yl)-5-(R)-[1,2,3]triazol-1-ylmethyl-
oxazolidin-2-one

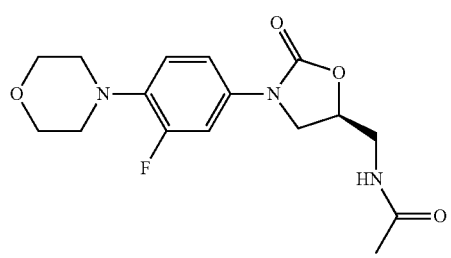

Linezolid or (S)-N-[[3-[3-Fluoro-4-(4-morpholinyl)phenyl]-2-
oxo-5-oxazolidinyl] methyl]-acetamide

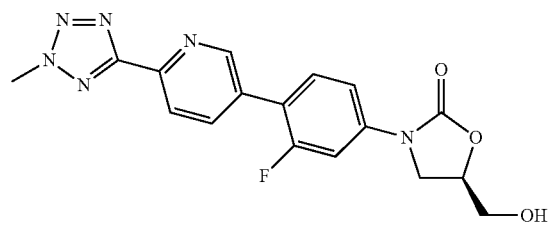

Torezolid, TR-701, tedizolid of (5R)-3-{3-fluoro-4-[6-(2-
methyl-2H-tetrazol-5-yl)pyridin-3-yl]phenyl}-5-
(hydroxymethyl)-1,3-oxazolidin-2-one or a pharmaceutically acceptable salt, ester, or prodrug thereof. An example of a salt would be the monohydrochloride salt of the foregoing oxazolidinones A, B, C, and D.

For compound C, above, the following numbering convention can be used in which the triazole ring is attached at the "4" position to the remainder of the compound, and where the remaining carbon atom at position "5" of the triazole ring is unsubstituted, i.e. where it has a hydrogen, is as follows:

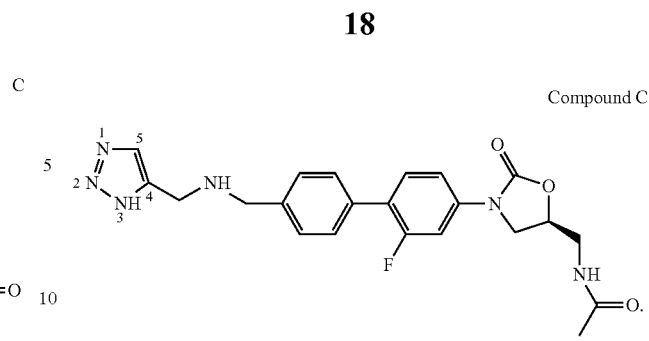

Compound C

It should be recognized that the triazole ring is a 5-membered heteroaromatic ring and that the location of the two double bonds drawn in most representations is an arbitrary depiction of one of the multiple structures that can be drawn, and is used for convenience and not intended as a limitation. In fact, five different structures, sometimes called tautomeric structures, can be drawn to depict a 1,2,3-triazole. These tautomeric structures can be indicated with double-headed arrows between each structure, indicating that the molecules so represented are in equilibrium with each other. For example, for Compound C, the following tautomeric structures can be drawn:

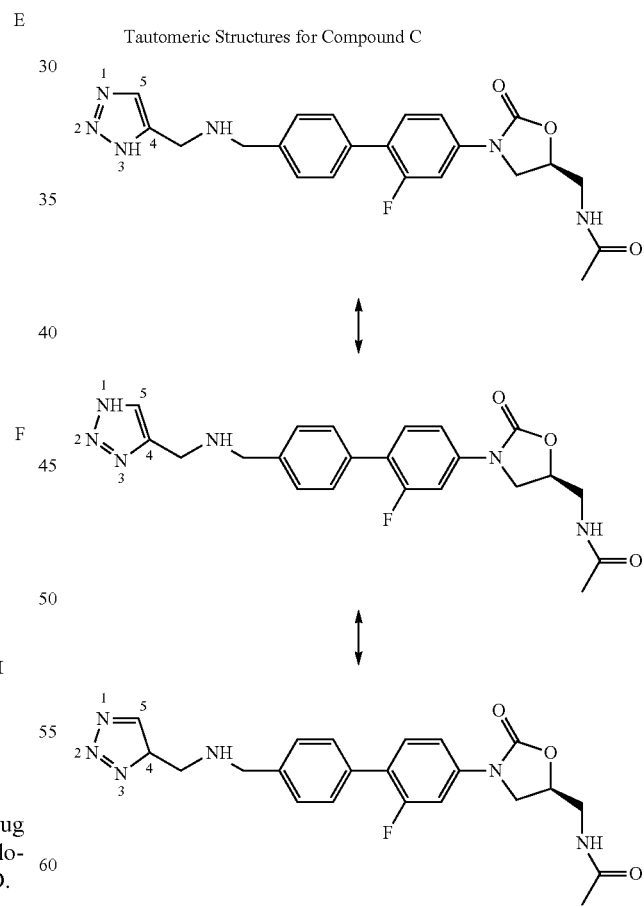

Tautomeric Structures for Compound C

-continued

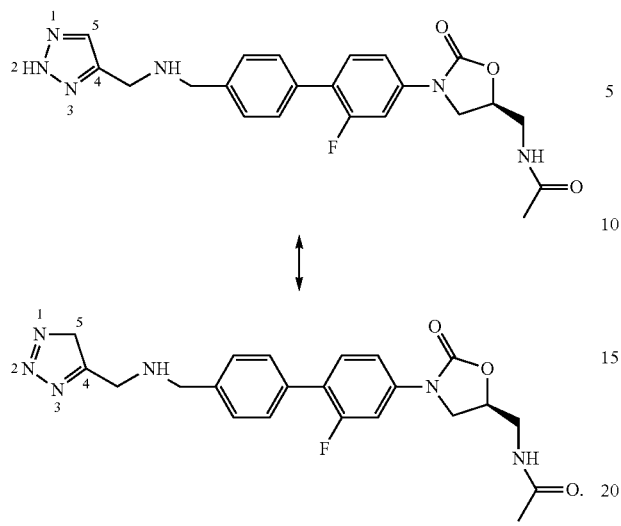

Further disclosure on oxazolidinones useful herein and compounds such as oxazolidinones C and D are found in U.S. Pat. No. 6,969,726 B2, to Lou et al., issued Nov. 29, 2005, cited above. Compound C, is also known by the chemical name: Acetamide, N-[[(5S)-3-(2-Fluoro-4'-[[(1H-1,2,3-triazole-4-ylmethyl)-amino]methyl][1,1'-biphenyl]-4-yl]-2-oxo-5-oxazolidinyl]-methyl]-, and has the CAS registry number 869884-78-6. The monohydrochloride salt of compound C is also known by the chemical name: Acetamide, N-[[(5S)-3-(2-Fluoro-4'-[[(1H-1,2,3-triazole-4-ylmethyl)-amino]methyl][1,1'-biphenyl]-4-yl]-2-oxo-5-oxazolidinyl]-methyl]-, monohydrochloride, and has the CAS registry number 869884-77-5.

Tedizolid is disclosed in U.S. Pat. No. 7,816,376, U.S. Patent Application Publication No. US 2009/0192197 and International Patent Application Publication No. WO 2004/058886, the contents of the foregoing of which are all incorporated herein by reference in their entireties.

These and other oxazolidinones relate to a compound having the formula:

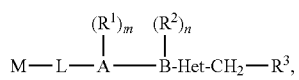

or a pharmaceutically acceptable salt, ester or prodrug thereof, wherein:
A is selected from the group consisting of:
  phenyl, pyridyl, pyrazinyl, pyrimidinyl, and pyridazinyl;
B is selected from the group consisting of:
  phenyl, pyridyl, pyrazinyl, pyrimidinyl, and pyridazinyl;
Het-CH$_2$—R$^3$ is selected from the group consisting of:

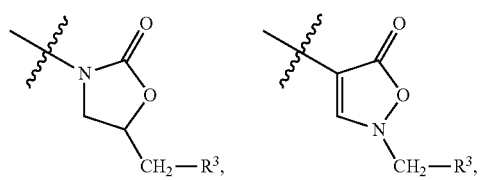

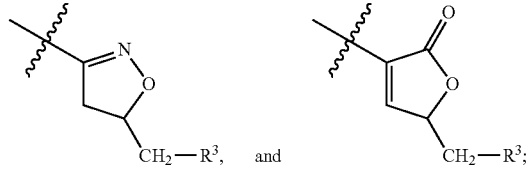

M is selected from the group consisting of:
  a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur,
    wherein a) or b) optionally is substituted with one or more R$^5$ groups;
M-L is selected from the group consisting of:
  a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X—X—, i) M-L$^1$-X—X—, j) M-X—X-L$^2$, and k) M-L$^1$-X—X-L$^2$, wherein
X, at each occurrence, independently is selected from the group consisting of:
  a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—,
  q) —NR$^4$C(O)NR$^4$— r) —NR$^4$C(NR$^4$)NR$^4$—, and s)

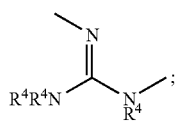

L$^1$ is selected from the group consisting of:
  a) C$_{1-6}$alkyl, b) C$_{2-6}$alkenyl, and c) C$_{2-6}$alkynyl, wherein any of a)-c) optionally is substituted with one or more R$^5$ groups; and
L$^2$ is selected from the group consisting of:
  a) C$_{1-6}$alkyl, b) C$_{2-6}$alkenyl, and c) C$_{2-6}$alkynyl, wherein any of a)-c) optionally is substituted with one or more R$^5$ groups;
R$^1$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$,
  y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;
R$^2$, at each occurrence, independently is selected from the group consisting of:
  a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)

R⁴, u) —C(S)NR⁴R⁴, v) —NR⁴C(S)R⁴, w) —OC(S)NR⁴R⁴, x) —NR⁴C(S)OR⁴, y) —NR⁴C(S)NR⁴R⁴, z) —NR⁴C(NR⁴)NR⁴R⁴, aa) —S(O)$_p$R⁴, bb) —SO₂NR⁴R⁴, and cc) R⁴;

R³ is selected from the group consisting of:
- a) —OR⁴, b) —NR⁴R⁴, c) —C(O)R⁴, d) —C(O)OR⁴,
- e) —OC(O)R⁴, f) —C(O)NR⁴R⁴, g) —NR⁴C(O)R⁴,
- h) —OC(O)NR⁴R⁴, i) —NR⁴C(O)OR⁴, j) —NR⁴C(O)NR⁴R⁴,
- k) —C(S)R⁴, l) —C(S)OR⁴, m) —OC(S)R⁴, n) —C(S)NR⁴R⁴, o) —NR⁴C(S)R⁴,
- p) —OC(S)NR⁴R⁴, q) —NR⁴C(S)OR⁴, r) —NR⁴C(S)NR⁴R⁴, s) —NR⁴C(NR⁴)NR⁴R⁴, t) —S(O)$_p$R⁴, u) —SO₂NR⁴R⁴, and v) R⁴;

R⁴, at each occurrence, independently is selected from the group consisting of:
- a) H, b) C$_{1-6}$ alkyl, c) C$_{2-6}$alkenyl, d) C$_{2-6}$alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$alkyl,
- h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$alkenyl, n) —C(O)O—C$_{2-6}$alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
  wherein any of b)-p) optionally is substituted with one or more R⁵ groups;

R⁵, at each occurrence, is independently selected from the group consisting of:
- a) F, b) Cl, c) Br, d) I, e) =O, f) =S, g) =NR⁶, h) =NOR⁶, i) =N—NR⁶R⁶, j) —CF₃, k) —OR⁶, l) —CN, m) —NO₂, n) —NR⁶R⁶, o) —C(O)R⁶, p) —C(O)OR⁶, q) —OC(O)R⁶, r) —C(O)NR⁶R⁶, s) —NR⁶C(O)R⁶, t) —OC(O)NR⁶R⁶, u) —NR⁶C(O)OR⁶,
- v) —NR⁶C(O)NR⁶R⁶, w) —C(S)R⁶, x) —C(S)OR⁶, y) —OC(S)R⁶, z) —C(S)NR⁶R⁶, aa) —NR⁶C(S)R⁶, bb) —OC(S)NR⁶R⁶, cc) —NR⁶C(S)OR⁶, dd) —NR⁶C(S)NR⁶R⁶, ee) —NR⁶C(NR⁶)NR⁶R⁶, ff) —S(O)$_p$R⁶, gg) —SO₂NR⁶R⁶, and hh) R⁶;

R⁶, at each occurrence, independently is selected from the group consisting of:
- a) H, b) C$_{1-6}$ alkyl, c) C$_{2-6}$alkenyl, d) C$_{2-6}$alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$alkyl,
- h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$alkyl, m) —C(O)O—C$_{2-6}$alkenyl, n) —C(O)O—C$_{2-6}$alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
  wherein any of b)-p) optionally is substituted with one or more R⁷ groups;

R⁷, at each occurrence, independently is selected from the group consisting of:
- a) F, b) Cl, c) Br, d) I, e) =O, f) =S, g) =NR⁸, h) =NOR⁸, i) =N—NR⁸R⁸, j) —CF₃, k) —OR⁸, l) —CN, m) —NO₂, n) —NR⁸R⁸, o) —C(O)R⁸, p) —C(O)OR⁸, q) —OC(O)R⁸, r) —C(O)NR⁸R⁸, s) —NR⁸C(O)R⁸, t) —OC(O)NR⁸R⁸, u) —NR⁸C(O)OR⁸,
- v) —NR⁸C(O)NR⁸R⁸, w) —C(S)R⁸, x) —C(S)OR⁸, y) —OC(S)R⁸, z) —C(S)NR⁸R⁸, aa) —NR⁸C(S)R⁸, bb) —OC(S)NR⁸R⁸, cc) —NR⁸C(S)OR⁸, dd) —NR⁸C(S)NR⁸R⁸, ee) —NR⁸C(NR⁸)NR⁸R⁸, ff) —S(O)$_p$R⁸, gg) —SO₂NR⁸R⁸, hh) C$_{1-6}$alkyl,
- ii) C$_{2-6}$alkenyl, jj) C$_{2-6}$alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur,
  wherein any of hh)-ll) optionally is substituted with one or more moieties selected from the group consisting of R⁸, F, Cl, Br, I, —CF₃, —OR⁸, —SR⁸, —CN, —NO₂, —NR⁸R⁸, —C(O)R⁸, —C(O)OR⁸, —OC(O)R⁸, —C(O)NR⁸R⁸, —NR⁸C(O)R⁸, —OC(O)NR⁸R⁸, —NR⁸C(O)OR⁸, —NR⁸C(O)NR⁸R⁸, —C(S)R⁸, —C(S)OR⁸, —OC(S)R⁸, —C(S)NR⁸R⁸, —NR⁸C(S)R⁸, —OC(S)NR⁸R⁸, —NR⁸C(S)OR⁸, —NR⁸C(S)NR⁸R⁸, —NR⁸C(NR⁸)NR⁸R⁸, —SO₂NR⁸R⁸, and —S(O)$_p$ R⁸;

R⁸, at each occurrence, independently is selected from the group consisting of:
- a) H, b) C$_{1-6}$ alkyl, c) C$_{2-6}$alkenyl, d) C$_{2-6}$alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$alkyl,
- h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$alkenyl, n) —C(O)O—C$_{2-6}$alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
  wherein any of b)-p) optionally is substituted with one or more moieties selected from the group consisting of F, Cl, Br, I, —CF₃, —OH, —OCH₃, —SH, —SCH₃, —CN, —NO₂, —NH₂, —NHCH₃, —N(CH₃)₂, —C(O)CH₃, —C(O)OCH₃, —C(O)NH₂, —NHC(O)CH₃, —SO₂NH₂, —SO₂NHCH₃, —SO₂N(CH₃)₂, and —S(O)$_p$ CH₃;

m, at each occurrence, independently is 0, 1, 2, 3, or 4;
n, at each occurrence, independently is 0, 1, 2, 3, or 4; and p, at each occurrence, independently is 0, 1, or 2.

Particular embodiments of the disclosure include compounds having the formula:

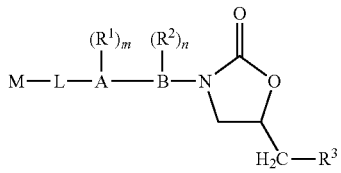

or a pharmaceutically acceptable salt, ester or prodrug thereof, wherein A, B, L, M, $R^1$, $R^2$, $R^3$, m, and n are defined above.

Other embodiments include compounds having the formula:

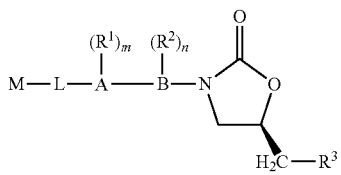

or a pharmaceutically acceptable salt, ester or prodrug thereof, wherein A, B, L, M, $R^1$, $R^2$, $R^3$, m, and n are defined as described above.

Particular compounds include those where A is selected from the group consisting of phenyl and pyridyl; B is selected from the group consisting of phenyl and pyridyl; m is 0, 1, or 2; and n is 0, 1, or 2.

In some embodiments, A-B is:

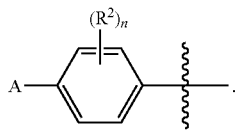

wherein A, $R^2$, and n are defined as described above. In particular embodiments, A-B is:

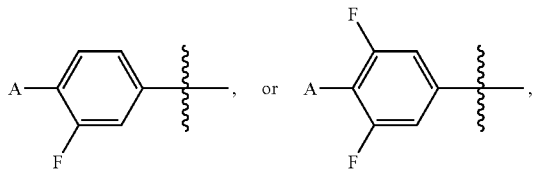

wherein A is defined as described above.

In various embodiments, A-B is:

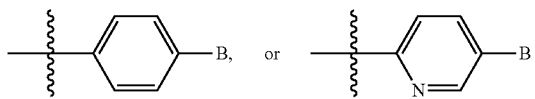

wherein B is defined as described in above.

In some embodiments, $R^3$ is —NHC(O)$R^4$. Particular compounds according to these embodiments include those where $R^4$ is —CH$_3$. In other embodiments, $R^3$ is:

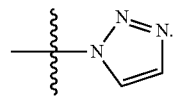

Particular embodiments of the disclosure include compounds having the formula:

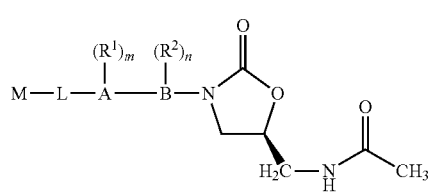

or a pharmaceutically acceptable salt, ester or prodrug thereof, wherein A, B, L, M, $R^1$, $R^2$, m, and n are defined as described above.

Other embodiments of the disclosure include compounds having the formula:

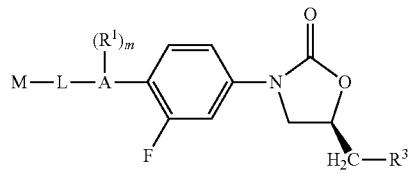

or a pharmaceutically acceptable salt, ester or prodrug thereof, wherein A, L, M, $R^1$, $R^3$, and m are defined as described above.

Still other embodiments of the disclosure include compounds having the formula:

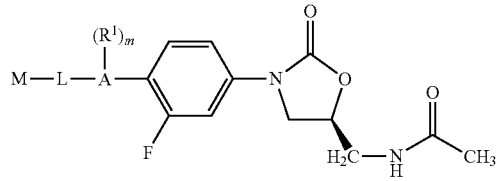

or a pharmaceutically acceptable salt, ester or prodrug thereof, wherein A, L, M, $R^1$, and m are defined as described above.

Some embodiments of the disclosure include compounds having the formula:

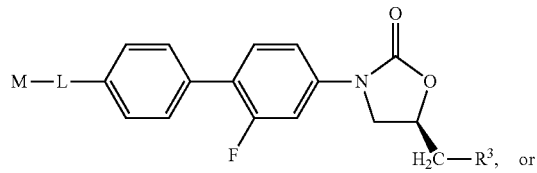

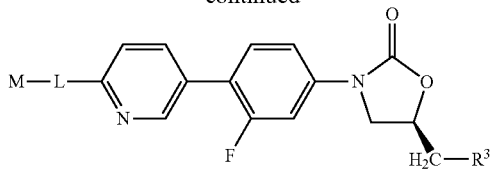

or a pharmaceutically acceptable salt, ester or prodrug thereof, wherein L, M, and R³ are defined as described above. Particular compounds according to these embodiments include those wherein R³ is —NHC(O)CH₃.

Other embodiments of the disclosure include compounds having the formula:

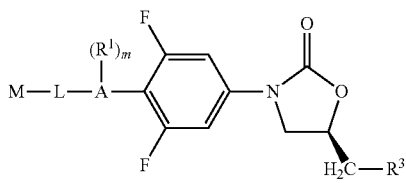

or a pharmaceutically acceptable salt, ester or prodrug thereof, wherein A, L, M, R¹, R³, and m are defined as described above.

Still other embodiments of the disclosure include compounds having the formula:

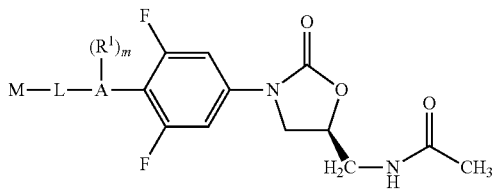

or a pharmaceutically acceptable salt, ester or prodrug thereof, wherein A, L, M, R¹, and m are defined as described above.

Some embodiments of the disclosure include compounds having the formula:

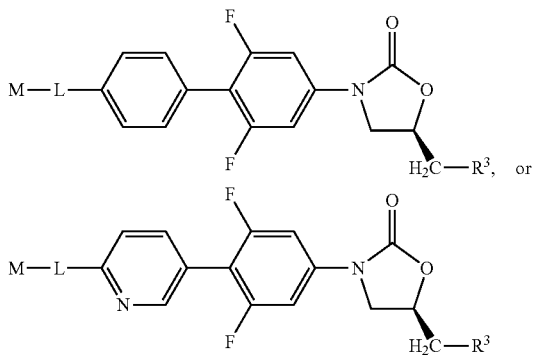

or a pharmaceutically acceptable salt, ester or prodrug thereof, wherein L, M, and R³ are defined as described above. Particular compounds according to these embodiments include those wherein R³ is —NHC(O)CH₃.

In some embodiments, M-L is M-L¹, and L¹ is $C_{1-6}$ alkyl. In particular embodiments, M-L¹ is M-CH₂—.

In other embodiments, M-L is M-L¹-X-L², and X is —NR⁴—. In particular compounds according to these embodiments, X is —NH—, —N(O)—, or —N(OR⁴)—, where R⁴ is H or $C_{1-6}$ alkyl. Other compounds include those where X is

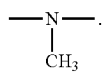

In certain compounds according to these embodiments, L¹ is $C_{1-6}$ alkyl, and L² is $C_{1-6}$ alkyl. In some embodiments, L¹ is —CH₂— and L² is —CH₂—. Particular examples of compounds according to these embodiments include those where M-L is M-CH₂—NH—CH₂— or

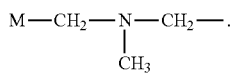

In still other embodiments, M-L is M-S-L¹-NR⁴-L², wherein L¹ is $C_{1-6}$ alkyl, and L² is $C_{1-6}$ alkyl. In particular compounds according to these embodiments, M-L is M-S—CH₂CH₂—NH—CH₂—.

In particular embodiments, M is selected from the group consisting of:
a) phenyl, b) pyridyl, c) pyrazinyl, d) pyrimidinyl, e) pyridazinyl, f) oxiranyl, g) aziridinyl, h) furanyl, i) thiophenyl, j) pyrrolyl, k) oxazolyl, l) isoxazolyl, m) imidazolyl, n) pyrazolyl, o) isothiazolyl, p) thiazolyl, q) triazolyl, r) tetrazolyl, s) indolyl, t) purinyl, u) benzofuranyl, v) benzoxazolyl,
w) benzisoxazolyl, x) quinolinyl, y) isoquinolinyl, z) quinoxalinyl,
aa) quinazolinyl, bb) cinnolinyl, cc) cyclopropyl, dd) cyclobutyl, ee) cyclopentyl, ff) cyclohexyl, gg) cycloheptyl, hh) oxetanyl, ii) tetrahydrofuranyl, jj) tetrahydropyranyl, kk) azetidinyl, ll) pyrrolidinyl, mm) piperidinyl, nn) thietanyl, oo) tetrahydrothiophenyl, pp) tetrahydrothiopyranyl, qq) piperazinyl, rr) quinuclidinyl, ss) 1-azabicyclo[2.2.1]hyeptanyl, tt) morpholinyl, uu) thiomorpholinyl, vv) thiooxomorpholinyl, ww) thiodioxomorpholinyl, and xx) benzothiophenyl
wherein any of a)-xx) optionally is substituted with one or more R⁵ groups. In particular embodiments, M is 4-isoxazolyl, [1,2,3]triazol-1-yl, 3H-[1,2,3]triazol-4-yl, 1H-tetrazol-5-yl, piperidin-1-yl, or pyrolidin-1-yl.

In some embodiments, A is phenyl, substituted phenyl, pyridyl, or substituted pyridyl. Under certain circumstances, when A is pyridin-4-yl substituted with M-L at the 2 position, M-L is not (imidazol-1-yl)methyl or (morpholin-4-yl)methyl.

In some embodiments, B is phenyl or substituted phenyl. More preferably, B is substituted phenyl. In some embodiments, substituents include halogens. Under certain circumstances, when B is unsubstituted phenyl, M-L is selected from the group consisting of M-X, M-L¹-X, M-L¹-X-L², M-X-L¹-X-L², M-X—X—, M-L¹-X—X—, M-X—X-L², and M-L¹-X—X-L². Under certain circumstances, when B is pyridin-2-yl substituted with A at the 5 position, M-L is selected from the group consisting of M-X, M-L$^1$-X, M-L$^1$-X-L$^2$, M-L$^1$-X-L$^2$-X, M-X—X—, M-X—X-L$^2$, and M-L$^1$-X—X-L$^2$.

Quinolones and Fluoroquinolones

Quinolone derivatives, such as pyridonecarboyxlic acid derivatives, useful herein are described, including their synthesis, formulation, and use, in U.S. Pat. No. 6,156,903, to Yazaki et al., issued Dec. 5, 2000 and its certificate of correction of Dec. 11, 2001; U.S. Pat. No. 6,133,284, to Yazaki et al., issued Oct. 17, 2000; U.S. Pat. No. 5,998,436, to Yazaki et al., issued Dec. 7, 1999 and its certificate of corrections of Jan. 23, 2001 and Dec. 17, 2002; PCT Application No. WO 2006/042034, to Abbott Laboratories, published Apr. 20, 2006, PCT Application No. WO 2006/015194, to Abbott Laboratories, published Feb. 9, 2006; PCT Application No. WO 01/34595, to Wakunaga Pharmaceutical Co., Ltd., published May 17, 2001; and PCT Application No. WO 97/11068, to Wakunaga Pharmaceutical Co., Ltd., published Mar. 27, 1997.

Pyridonecarboxylic acid derivatives of the methods, compositions, and uses of the present disclosure include compounds corresponding to the following structure (Pyridonecarboxylic Acid Derivative 1)

Pyridonecarboxylic Acid Derivative 1

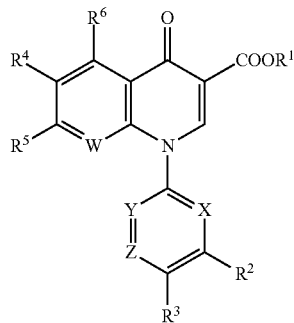

wherein R$^1$ represents a hydrogen atom or a carboxyl protective group; R$^2$ represents a hydroxyl group, a lower alkoxy group, or a substituted or unsubstituted amino group; R$^3$ represents a hydrogen atom or a halogen atom; R$^4$ represents a hydrogen atom or a halogen atom; R$^5$ represents a halogen atom or an optionally substituted saturated cyclic amino group; R$^6$ represents a hydrogen atom, a halogen atom, a nitro group, or an optionally protected amino group; X, Y and Z may be the same or different and respectively represent a nitrogen atom, CH or CR$^7$ (wherein R$^7$ represents a lower alkyl group, a halogen atom, or a cyano group), with the proviso that at least one of X, Y and Z represent a nitrogen atom, and W represents a nitrogen atom or CR$^8$ (wherein R$^8$ represents a hydrogen atom, a halogen atom, or a lower alkyl group), and with the proviso that when R$^1$ represents a hydrogen atom, R$^2$ represents an amino group, R$^3$ and R$^4$ represent a fluorine atom, R$^6$ represents a hydrogen atom, X represents a nitrogen atom, Y represents CR$^7$ (wherein R$^7$ represents a fluorine atom), Z represents CH, and W is CR$^8$ (wherein R$^8$ represents a chlorine atom), then R$^5$ is not a 3-hydroxyazetidine-1-yl group; or a pharmaceutically acceptable salt, ester, or prodrug thereof.

As described in the foregoing paragraph, when R$^1$ is a carboxyl protective group, it may be any carboxylate ester residue which cleaves relatively easily to generate the corresponding free carboxyl group. Exemplary carboxyl protective groups include those which may be eliminated by hydrolysis, catalytic reduction, and other treatments under mild conditions such as lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group; and aryl groups such as phenyl group and naphthyl group; and those which may be readily eliminated in the body such as lower alkanoyloxy lower alkyl groups such as acetoxymethyl group and pivaloyloxymethyl group; lower alkoxycarbonyloxy lower alkyl group such as methoxycarbonyloxymethyl group and 1-ethoxycarbonyloxyethyl group; lower alkoxymethyl group such as methoxymethyl group; lactonyl group such as phthalidyl; di-lower alkylamino lower alkyl group such as 1-dimethylaminoethyl group; and (5-methyl-2-oxo-1,3-dioxole-4-yl)methyl group.

It is noted that the substituents R$^1$, R$^2$, R$^3$, R$^4$, R$^5$, R$^6$, R$^7$, R$^8$, R$^9$, A, J$^1$, J$^2$, J$^3$, W, X, Y, Z, e, f, and g are defined herein for convenience with respect to the chemical structure for the pyridonecarboxylic acid derivatives, e.g., Pyridonecarboxylic Acid Derivative 1, and do not refer to other substituents for other compounds disclosed herein.

In other embodiments, the present disclosure relates to a method, composition, or use for a pyridonecarboxylic acid derivative of structure Pyridonecarboxylic Acid Derivative 1, wherein W is CR$^8$, wherein R$^8$ represents a hydrogen atom, a halogen atom, or a lower alkyl group.

In other embodiments, the present disclosure relates to a method, composition, or use for a pyridonecarboxylic acid derivative of structure Pyridonecarboxylic Acid Derivative 1, wherein R$^5$ is a group represented by the following formula (a) or (b):

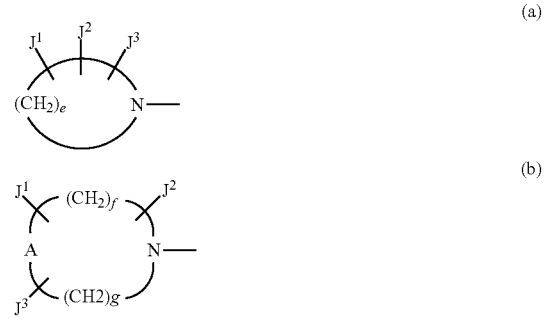

wherein A represents an oxygen atom, sulfur atom or NR$^9$ (wherein R$^9$ represents hydrogen atom or a lower alkyl group), e represents a number from 3 to 5, f represents a number from 1 to 3, g represents a number from 0 to 2, J$^1$, J$^2$ and J$^3$, which may be the same or different from one another, represent a hydrogen atom, hydroxyl group, lower alkyl group, amino lower alkyl group, amino group, lower alkylamino group, lower alkoxy group, or a halogen atom.

In other embodiments, the present disclosure relates to a method, composition, or use for a pyridonecarboxylic acid derivative of structure Pyridonecarboxylic Acid Derivative 1, wherein R$^5$ is a group represented by formula (a).

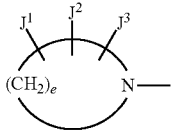

(a)

In other embodiments, the present disclosure relates to a method, composition, or use for a pyridonecarboxylic acid derivative of structure Pyridonecarboxylic Acid Derivative 1, wherein e in the formula (a) is 3 or 4.

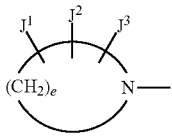

(a)

In other embodiments, the present disclosure relates to a method, composition, or use for a pyridonecarboxylic acid derivative of structure Pyridonecarboxylic Acid Derivative 1, wherein $R^1$ is a hydrogen atom; $R^2$ is an amino group, lower alkylamino group, or a di-lower alkylamino group; $R^3$ is a halogen atom; $R^4$ is a halogen atom; $R^6$ is hydrogen atom; X is a nitrogen atom; Y and Z are CH or $CR^7$ (wherein $R^7$ is a lower alkyl group or a halogen atom); and W is $CR^8$ (wherein $R^8$ is a halogen atom or a lower alkyl group).

In other embodiments, the present disclosure relates to a method, composition, or use for a pyridonecarboxylic acid derivative of structure Pyridonecarboxylic Acid Derivative 1, wherein $R^2$ is amino group; $R^3$ is fluorine atom; $R^4$ is a fluorine atom; Y is CF; Z is CH; W is $CR^8$ (wherein $R^8$ is a chlorine atom, bromine atom or a methyl group), and e in formula (a) is 3.

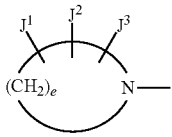

(a)

In other embodiments, the present disclosure relates to a method, composition, or use wherein said pyridonecarboxylic acid corresponds to the following structure:

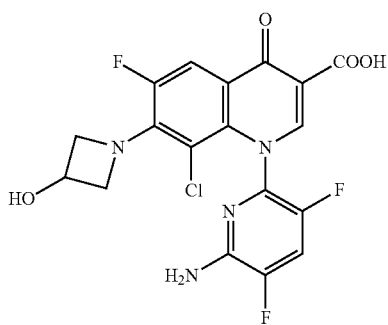 [SMILES: Nc1nc(-n2cc(C(=O)O)c(=O)c3cc(F)c(N4CC(O)C4)c(Cl)c32)c(F)cc1F]

or a pharmaceutically acceptable salt, ester, or prodrug thereof. This foregoing pyridonecarboxylic acid is also known by the publicly disclosed code names ABT-492 and WQ 3034 and also by the chemical name 1-(6-amino-3,5-difluoro-2-pyridinyl)-8-chloro-6-fluoro-1,4-dihydro-7-(3-hydroxy-1-azetidinyl)-4-oxo-3-quinolinecarboxylic acid or 1-(6-amino-3,5-difluoro-2-pyridinyl)-8-chloro-6-fluoro-1,4-dihydro-7-(3-hydroxyazetidin-1-yl)-4-oxo-3-quinolinecarboxylic acid. This carboxylic acid form of the compound corresponds to the CAS registry number 189279-58-1. Furthermore, WO 2006/042034, cited above discloses the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt)] and the trihydrate of the D-glucitol salt of this compound [D-glucitol 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt)]. The D-glucitol salt and the D-glucitol salt trihydrate correspond to the CAS registry numbers 352458-37-8 and 883105-02-0, respectively. D-glucitol corresponds to the CAS registry number 6284-40-8. WO 2006/042034 also discloses a crystalline form of the D-glucitol salt characterized when measured at about 25° C. with Cu—Kα radiation, by the powder diffraction pattern shown in FIG. 1 of WO 2006/042034 and a crystalline form of the D-glucitol salt trihydrate when measured at about 25° C. with Cu—Kα radiation, by the powder diffraction pattern shown in FIG. 2 of WO 2006/042034. These D-glucitol salts are useful in the present disclosure. Also, see A. R. Haight et al., "Synthesis of the Quinolone ABT-492: Crystallizations for Optimal Processing", Organic Process Research & Development (2006), 10(4), 751-756.

Other quinolone compounds useful herein, include fluoroquinolones such asbalofloxacin, ciprofloxacin, clinafloxacin, enoxacin, fleroxacin, gatifloxacin, gemifloxacin, grepafloxacin, levofloxacin, lomefloxacin, moxifloxacin, nadifloxacin, norfloxacin, ofloxacin, pazufloxacin, pefloxacin, prulifloxacin, rufloxacin, sitafloxacin, sparfloxacin, temafloxacin, tosufloxacin, and trovafloxacin.

Garenoxacin and its pharmaceutically acceptable salts, esters, and prodrugs thereof, can be used in the methods, compositions, and uses of the present disclosure. Garenoxacin is also known as 1-cyclopropyl-8-(difluoromethoxy)-7-(1R)-(1-methyl-2,3-dihydro-1H-5-isoinodyl)-4-oxo-1,4-dihydro-3-quinolinecarboxylic acid methanesulfonate monohydrate and by the publicly disclosed code names T-3811 and BM 284756. See M. Takahata et al., "In Vitro and In Vivo Antimicrobial Activities of T-3811ME, a Novel Des-F(6)-Quinolone", Antimicrobial Agents and Chemotherapy, vol. 43, no. 5, pp. 1077-1084 (1999); U.S. Pat. No. 6,025,370, to Todo et al, issued Feb. 15, 2000; and U.S. Pat. No. 5,935,952, to Todo et al., issued Aug. 10, 1999 and its certificate of correction of Dec. 5, 2000.

Gatifloxacin and its pharmaceutically acceptable salts, esters, and prodrugs thereof, can be used in the methods, compositions, and uses of the present disclosure. Gatifloxacin is sold under the trade name or proprietary Tequin. See U.S. Pat. No. 6,589,955 B2, to Raghavan et al., issued Jul. 8, 2003; U.S. Pat. No. 5,880,283, to Matsumoto et al., issued Mar. 9, 1999; and U.S. Pat. No. 4,980,470, to Masuzawa et al., issued Dec. 25, 1990 and its certificate of correction of Aug. 11, 1992.

Gemifloxacin and its pharmaceutically acceptable salts, esters, and prodrugs thereof, can be used in the methods, compositions, and uses of the present disclosure. Gemifloxacin is sold under the trade name or proprietary Factive. See U.S. Pat. No. 6,803,376 B1, to Appelbaum et al., issued Oct. 12, 2004; U.S. Pat. No. 6,723,734 B2, to Kim et al., issued Apr. 20, 2004; U.S. Pat. No. 6,455,540 B1, to Citron et al., issued Sep. 24, 2002; U.S. Pat. No. 6,340,689 B1, to Dubois et al., issued Jan. 22, 2002 and its certificate of correction of Jun. 18, 2002; U.S. Pat. No. 6,331,550 B1, to Citron et al., issued Dec. 18, 2001; U.S. Pat. No. 6,262,071 B1, to Crabb et al., issued Jul. 17, 2001; U.S. Pat. No. 5,962,468, to Hong et al., issued Oct. 5, 1999 and its certificate of correction of May 9, 2000; U.S. Pat. No. 5,776,944, to Hong et al., issued Jul. 7, 1998; and U.S. Pat. No. 5,633,262, to Hong et al., issued May 27, 1997.

Levofloxacin and its pharmaceutically acceptable salts, esters, and prodrugs thereof, can be used in the methods, compositions, and uses of the present disclosure. Levofloxacin is sold under the trade name or proprietary Levaquin. See U.S. Pat. No. 5,053,407, to Hayakawa et al., issued Oct. 1, 1991 and its certificate of correction of Sep. 27, 1994.

Moxifloxacin and its pharmaceutically acceptable salts, esters, and prodrugs thereof, can be used in the methods, compositions, and uses of the present disclosure. Moxifloxacin is sold under the trade name or proprietary Avelox. See U.S. Pat. No. 5,849,752, to Grunenberg et al., issued Dec. 15, 1998; U.S. Pat. No. 5,607,942, to Petersen et al., issued Mar. 4, 1997; and U.S. Pat. No. 4,990,517, to Petersen et al., issued Feb. 5, 1991 and its certificate of correction of Apr. 25, 1995.

Benzoheterocyclic Compounds

Benzoheterocyclic compounds useful herein are described, including their synthesis, formulation, and use, in U.S. Pat. No. 6,753,333 B2, to De Souza et al., issued Jun. 22, 2004; U.S. Pat. No. 6,750,224 B1, to Patel et al, issued Jun. 15, 2004 and its certificate of correction of Nov. 2, 2004; U.S. Pat. No. 6,664,267 B1, to de Souza et al., issued Dec. 16, 2003; U.S. Pat. No. 6,608,078 B2, to De Souza et al., issued Aug. 19, 2003; U.S. Pat. No. 6,514,986 B2 to De Souza et al., issued Feb. 4, 2003; U.S. Pat. No. 4,552,879 to Ishikawa et al., issued Nov. 12, 1985; and U.S. Pat. No. 4,399,134 to Ishikawa et al., issued Aug. 16, 1983.

Benzoheterocyclic compounds of the methods, compositions, and uses of the present disclosure include compounds corresponding to the following structure (Benzoheterocyclic Compound I)

Benzoheterocyclic Compound I

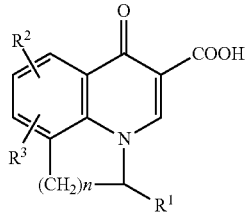

wherein $R^1$ represents a hydrogen atom or a lower alkyl group; $R^2$ represents a hydrogen atom or a halogen atom; $R^3$ represents a 1-pyrrolidinyl group which may be substituted with a hydroxymethyl group, a 1,2,5,6-tetrahydro-1-pyridyl group, or a group of the formula

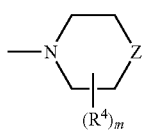

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is an integer of 1 or 2; or a pharmaceutically acceptable salt ester or prodrug thereof.

It is noted that the substituents $R^1$, $R^2$, $R^3$, $R^4$, Z, m, and n are defined herein for convenience with respect to the chemical structure for the benzoheterocyclic compounds, e.g., benzoheterocyclic compound (I) and do not refer to other substituents for other compounds of the present disclosure.

In other embodiments, the present disclosure relates to a method, composition, or use for a benzoheterocyclic of structure Benzoheterocyclic Compound I, wherein n is 2.

In other embodiments, the present disclosure relates to a method, composition, or use for a benzoheterocyclic of structure Benzoheterocyclic Compound I, wherein n is 1.

In other embodiments, the present disclosure relates to a method, composition, or use for a benzoheterocyclic of structure Benzoheterocyclic Compound I, wherein $R^3$ represents a group of the formula

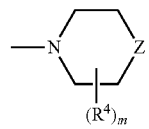

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1.

In other embodiments, the present disclosure relates to a method, composition, or use for a benzoheterocyclic of structure Benzoheterocyclic Compound I, wherein $R^3$ represents a 1-pyrrolidinyl group which may be substituted with a hydroxymethyl group or a 1,2,5,6-tetrahydro-1-pyridyl group.

In other embodiments, the present disclosure relates to a method, composition, or use for a benzoheterocyclic of structure Benzoheterocyclic Compound I, wherein $R^4$ represents a hydrogen atom, a hydroxy group or a lower alkanoyloxy group and the position at which the group of the formula

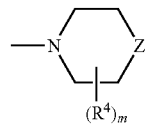

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1, is attached is the 8-position.

In other embodiments, the present disclosure relates to a method, composition, or use for a benzoheterocyclic of structure Benzoheterocyclic Compound I, wherein $R^4$ represents a lower alkyl group, a lower alkoxy group, a phenyl-lower alkyl group, an amino group which may be substituted with a lower alkyl group or a lower alkanoyl group, an oxo group, a carbamoyl group, and the position at which the group of the formula

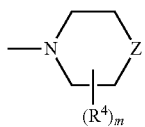

where $R^4$ represents a hydrogen atom, a lower alkyl group, a lower alkoxy group, a hydroxy group, a phenyl-lower alkyl group, a lower alkanoyloxy group, an amino group which may be substituted with a lower alkyl group or a lower alkanoyl group, an oxo group, or a carbamoyl group; Z represents an oxygen atom, a sulfur atom or a methylene group; and m is 1 or 2; and n is 1, is attached is the 8-position.

In other embodiments, the present disclosure relates to a method, composition, or use for a benzoheterocyclic of structure Benzoheterocyclic Compound I, wherein $R^2$ represents a halogen atom.

In other embodiments, the present disclosure relates to a method, composition, or use for a benzoheterocyclic of structure Benzoheterocyclic Compound I, wherein $R^2$ represents a hydrogen atom.

In other embodiments, the present disclosure relates to a method, composition, or use for a benzoheterocyclic of structure Benzoheterocyclic Compound I, wherein $R^2$ represents a fluorine atom and the position at which the fluorine atom is attached is the 9-position.

In other embodiments, the present disclosure relates to a method, composition, or use for a benzoheterocyclic of structure Benzoheterocyclic Compound I, wherein $R^2$ represents a chlorine atom and the position at which the fluorine atom is attached is the 9-position.

In other embodiments, the present disclosure relates to a method, composition, or use for a benzoheterocyclic of structure Benzoheterocyclic Compound I, wherein $R^1$ represents a lower alkyl group.

In other embodiments, the present disclosure relates to a method, composition, or use for a benzoheterocyclic of structure Benzoheterocyclic Compound I, wherein $R^1$ represents a methyl group.

In other embodiments, the present disclosure relates to a method, composition, or use for a benzoheterocyclic of structure Benzoheterocyclic Compound I, wherein $R^2$ represents a fluorine atom attached to the 9-position and $R^1$ represents a methyl group.

In other embodiments, the present disclosure relates to a method, composition, or use for a benzoheterocyclic of structure Benzoheterocyclic Compound I, wherein $R^1$ represents a methyl group, $R^2$ represents a fluorine atom attached to the 9-position and the position at which the group represented by $R^3$ is attached is the 8-position.

In other embodiments, the present disclosure relates to a method, composition, or use for a benzoheterocyclic of structure Benzoheterocyclic Compound I, wherein the position at which $R^3$ is attached is the 9-position.

In other embodiments, the present disclosure relates to a method, composition, or use for a benzoheterocyclic of structure Benzoheterocyclic Compound I, wherein $R^1$ represents a methyl group, $R^2$ represents a fluorine atom attached to the 8-position.

In other embodiments, the present disclosure relates to a method, composition, or use for a benzoheterocyclic of structure Benzoheterocyclic Compound I, wherein $R^1$ represents a methyl group, $R^2$ represents a chlorine atom attached to the 8-position.

In other embodiments, the present disclosure relates to a method, composition, or use wherein said benzoheterocyclic compound is 9-fluoro-8-(4-hydroxy-1-piperidyl)-5-methyl-6,7-dihydro-1-oxo-1H,5H-benzo[i,j]quinolizine-2-carboxylic acid or a pharmaceutically acceptable salt, ester, or prodrug thereof.

In other embodiments, the present disclosure relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid or a pharmaceutically acceptable salt, ester, or prodrug thereof. The foregoing compound is also known by the chemical name nadifloxacin.

In other embodiments, the present disclosure relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt.

In other embodiments, the present disclosure relates to a method, composition, or use wherein said benzoheterocyclic compound is a specific polymorph or crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt.

In other embodiments, the present disclosure relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 10.16, 11.78, 12.52, 16.00, 18.94, 19.66, 20.36, 21.28, 21.92, 22.52, 24.74, 25.28, 30.74.

In other embodiments, the present disclosure relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 18.28, 18.8, 19.8, 20.12, 20.62, 21.10, 21.44, 21.88, 22.6, 23.02.

In other embodiments, the present disclosure relates to a method, composition, or use wherein said benzoheterocyclic compound is S-(−)-9-fluoro-6,7-dihydro-8-(4-hydroxypiperidin-1-yl)-5-methyl-1-oxo-1H,5H-benzo[i,j]quinolizine-2-carboxylic acid arginine salt having the following X-ray diffraction data: (2θ): 14.02±0.2, 14.82±0.2, 19.28±0.2, 22.12±0.2, 22.96±0.2, 23.46±0.2, 28.36±0.2.

With respect to specific polymorph or crystalline forms of the benzoheterocyclic compounds, examples being the arginine salts, a publicly disclosed code name for such a compound is WCK 771.

Beta-Lactams

Beta-lactams, for example carbapenems, examples of which are carbapenems with a 7-acylated imidazo[5-1,b]thiazole-2-yl group directly attached to the carbapenem moiety of the C-2 position, useful herein are described, including their synthesis, formulation, and use, in M. Kurazano et al., "In Vitro Activities of ME1036 (CP5609), a Novel Parenteral Carbapenem, Against Methicillin-Resistant Staphylococci", Antimicrobial Agents and Chemotherapy, vol. 48, no. 8, pp. 2831-2837 (August 2004); U.S.

Patent Application Publication No. US 2004/0038967 A1, to Kano et al., published Feb. 26, 2004; PCT Application No. WO 2004/055027, to Meiji Seika Kaisha, Ltd., published Jul. 1, 2004; and PCT Application No. WO 02/042312, to Meiji Seika Kaisha, Ltd., published May 30, 2002.

Beta-lactam compounds of the methods, compositions, and uses of the present disclosure include compounds corresponding to the following structure (Beta-Lactam I)

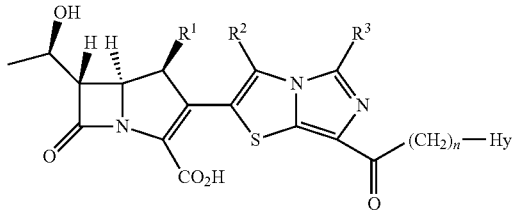

wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; lower cycloalkyl; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; carbamoyl; aryl optionally substituted by amino optionally substituted by one or two lower alkyl groups; lower alkylthio wherein the alkyl portion of lower alkylthio is optionally substituted by amino, hydroxyl, azide, a halogen atom, cyano, carbamoyl, formylamino, lower alkylcarbonylamino, aminosulfonylamino, or lower alkylthio; morpholinyl; lower alkylsulfonyl; or formyl; n is an integer of 0 to 4, and Hy represents a four- to seven-membered monocyclic or nine- or ten-membered bicyclic saturated or unsaturated heterocyclic group having one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom; hydroxyl; carbamoyl; carboxylmethyl-substituted carbamoyl; amino; N,N-di-lower alkylamino; aryl optionally substituted by amino; a monocyclic or bicyclic heterocyclic group containing one or more hetero-atoms selected from nitrogen, oxygen, and sulfur atoms, optionally substituted by aminosulfonyl or carboxyl; carboxyl; imino; lower alkoxycarbonyl; lower alkylcarbonyl; aminosulfonylamino; amino lower alkylthio; lower alkylsulfonyl; (N,N-di-lower alkylamino)sulfonylamino; N'—(N,N-di-lower alkylamino) sulfonyl-N'-lower alkylamino; halogenated lower alkylcarbonyl; N-aminosulfonylpiperidinyl; and cyano; lower alkylthio wherein one or more hydrogen atoms on the alkyl group are optionally substituted by a group selected from a halogen atom, hydroxyl, carbamoyl, amino, and aryl; lower alkylsulfonyl wherein one or more hydrogen atoms on the alkyl group are optionally substituted by a group selected from a halogen atom, hydroxyl, carbamoyl, amino, 1-iminoethylamino, and aryl; hydroxyl; lower alkoxy; hydroxyaminophenyl-substituted lower alkoxy; halogenated lower alkoxy; aminophenyl-substituted lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino) sulfonylamino-; (N,N-di-lower alkylamino)sulfonylamino; aryl; or a monocyclic or bicyclic heterocyclic group containing one or more hetero-atoms selected from nitrogen, oxygen, and sulfur atoms, optionally substituted by aminosulfonyl or carboxyl, or a pharmaceutically acceptable salt, ester or pro-drug thereof.

It is noted that the substituents $R^1$, $R^2$, $R^3$, Hy, and n are defined herein for convenience with respect to the chemical structure for the beta-lactams or carbapenems, e.g., Beta-Lactam I and Beta-Lactam II, and do not refer to other substituents for other compounds of the present disclosure.

In other embodiments, the present disclosure relates to a method, composition, or use for a beta-lactam of structure Beta-Lactam I, wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; aryl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio, n is an integer of 0 to 4, and Hy represents a four- to seven-membered monocyclic or nine- or ten-membered bicyclic saturated or unsaturated heterocyclic group containing one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more heteroatoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl; or a monocyclic or bicyclic heterocyclic group containing one or more heteroatoms selected from nitrogen, oxygen, and sulfur atoms.

In other embodiments, the present disclosure relates to a method, composition, or use of a beta-lactam of structure Beta-Lactam I wherein $R^1$ represents a hydrogen atom or methyl, $R^2$ and $R^3$, which may be the same or different, each represent a hydrogen atom, a halogen atom, optionally substituted lower alkyl, lower cycloalkyl, lower alkylcarbonyl, carbamoyl, optionally substituted aryl, optionally substituted lower alkylthio, morpholinyl, lower alkylsulfonyl, or formyl, n is an integer of 0 to 2, and Hy represents a group selected from optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinoliniumyl, optionally substituted isoquinolinyl, optionally substituted dihydroisoquinolinyl, optionally substituted piperazinyl, optionally substituted piperidinyl, optionally substituted indolyl, optionally substituted thiomorpholinyl, optionally substituted imidazolyl, and optionally substituted pyrrolidinyl.

In other embodiments, the present disclosure relates to a method, composition, or use of a beta-lactam of structure Beta-Lactam I wherein $R^1$ represents a hydrogen atom or methyl, $R^2$ and $R^3$, which may be the same or different, each represent a hydrogen atom, a halogen atom, optionally substituted lower alkyl, optionally substituted lower alkylcarbonyl, carbamoyl, aryl, or optionally substituted lower alkylthio, n is an integer of 0 to 4, and Hy represents a group selected from optionally substituted pyridinyl, optionally substituted pyridinium-yl, optionally substituted tetrahydropyridinyl, optionally substituted thiazolyl, optionally substituted pyrimidinyl, optionally substituted thienyl, optionally substituted quinolinyl, optionally substituted quinoliniumyl, and optionally substituted pyrrolidinyl.

In other embodiments, the present disclosure relates to Beta-lactam compounds of the methods, compositions, and uses of the present disclosure include compounds corresponding to the following structure (Beta-Lactam II)

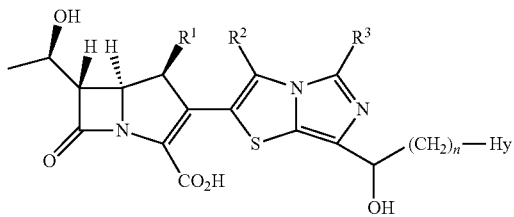

Beta-Lactam II wherein $R^1$ represents a hydrogen atom or methyl, $R^2$ and $R^3$, which may be the same or different, each represent a hydrogen atom; a halogen atom; lower alkyl optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; lower cycloalkyl; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, lower alkylthio, lower alkoxy, lower cycloalkyl, N,N-di-lower alkylamino, or N-carbamoyl lower alkyl-N,N-di-lower alkylammonino; carbamoyl; aryl optionally substituted by amino optionally substituted by one or two lower alkyl groups; lower alkylthio wherein the alkyl portion of lower alkylthio is optionally substituted by amino, hydroxyl, azide, a halogen atom, cyano, carbamoyl, formylamino, lower alkylcarbonylamino, aminosulfonylamino, or lower alkylthio; morpholinyl; lower alkylsulfonyl; or formyl; n is an integer of 0 to 4, and Hy represents a four- to seven-membered monocyclic or nine- or ten-membered bicyclic saturated or unsaturated heterocyclic group having one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom; hydroxyl; carbamoyl; carboxylmethyl-substituted carbamoyl; amino; N,N-di-lower alkylamino; aryl optionally substituted by amino; a monocyclic or bicyclic heterocyclic group containing one or more hetero-atoms selected from nitrogen, oxygen, and sulfur atoms, optionally substituted by aminosulfonyl or carboxyl; carboxyl; imino; lower alkoxycarbonyl; lower alkylcarbonyl; aminosulfonylamino; amino lower alkylthio; lower alkylsulfonyl; (N,N-di-lower alkylamino)sulfonylamino; N'—(N,N-di-lower alkylamino)sulfonyl-N'-lower alkylamino; halogenated lower alkylcarbonyl; N-aminosulfonylpiperidinyl; and cyano; lower alkylthio wherein one or more hydrogen atoms on the alkyl group are optionally substituted by a group selected from a halogen atom, hydroxyl, carbamoyl, amino, and aryl; lower alkylsulfonyl wherein one or more hydrogen atoms on the alkyl group are optionally substituted by a group selected from a halogen atom, hydroxyl, carbamoyl, amino, 1-iminoethylamino, and aryl; hydroxyl; lower alkoxy; hydroxyaminophenyl-substituted lower alkoxy; halogenated lower alkoxy; aminophenyl-substituted lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino-; (N,N-di-lower alkylamino)sulfonylamino; aryl; or a monocyclic or bicyclic heterocyclic group containing one or more hetero-atoms selected from nitrogen, oxygen, and sulfur atoms, optionally substituted by aminosulfonyl or carboxyl, or a pharmaceutically acceptable salt, ester, or pro-drug thereof.

In other embodiments, the present disclosure relates to a method, composition, or use of a beta-lactam of structure Beta-Lactam II, wherein $R^1$ represents a hydrogen atom or methyl, $R^2$ and $R^3$, which may be the same or different, each represent a hydrogen atom, a halogen atom, lower alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; aryl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio, n is an integer of 0 to 4, and Hy represents a four- to seven-membered monocyclic or nine- or ten-membered bicyclic saturated or unsaturated heterocyclic group containing one to four hetero-atoms selected from nitrogen, oxygen, and sulfur atoms, the saturated or unsaturated heterocyclic group represented by Hy is optionally substituted by a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms;

lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl; or a monocyclic or bicyclic heterocyclic group containing one or more heteroatoms selected from nitrogen, oxygen, and sulfur atoms.

In other embodiments, the present disclosure relates to a method, composition, or use of a beta-lactam of structure Beta-Lactam I or Beta-Lactam II, wherein the substituent on the lower alkyl and lower alkylcarbonyl groups optionally represented by $R^2$ and $R^3$ is hydroxyl, lower alkoxy, N,N-di-lower alkylamino, or N-carbamoyl lower alkyl-N,N-di-lower alkylammonino, the substituent on the aryl group optionally represented by $R^2$ and $R^3$ is N,N-di-lower alkylamino, the substituent on the lower alkylthio group optionally represented by $R^2$ and $R^3$ is amino, hydroxyl, or azide, and the substituent on the saturated or unsaturated heterocyclic ring represented by Hy is lower alkyl optionally substituted by carboxylmethyl-substituted carbamoyl, carbamoyl, phenyl, aminophenyl, N,N-di-lower alkylamino, amino, hydroxyl, morpholinyl, pyrrolidinyl, carboxyl, imino, amino lower alkylthio, lower alkoxycarbonyl, lower alkylcarbonyl, aminosulfonylamino, piperidinyl, lower alkylsulfonyl, (N,N-di-lower alkylamino)sulfonylamino, N'—(N,N-di-lower alkylamino)sulfonyl-N'-lower alkylamino, halogenated lower alkylcarbonyl, N-aminosulfonylpiperidinyl, or cyano; carbamoyl; pyridinyl; N-aminosulfonylpyrrolidinyl; 2-carboxypyrrolidinyl; phenyl; hydroxyl; lower alkoxy; hydroxyaminophenyl-substituted lower alkoxy; halogenated lower alkoxy; aminophenyl-substituted lower alkoxy; amino; carboxyl; lower alkylthio optionally substituted by amino; amino lower alkylthio; amino lower alkylsulfonyl; or 1-iminoethylamino lower alkylsulfonyl.

In other embodiments, the present disclosure relates to a method, composition, or use of a beta-lactam of structure Beta-Lactam I or Beta-Lactam II, wherein $R^1$ represents a hydrogen atom or methyl, $R^2$ and $R^3$ represent a hydrogen atom, n is 0 (zero), and Hy represents pyridinium-yl having carbamoylmethyl at its 1-position.

In other embodiments, the present disclosure relates to a method, composition, or use of a beta-lactam of structure Beta-Lactam I or Beta-Lactam II, wherein n is 0 (zero).

In other embodiments, the present disclosure relates to a method, composition, or use of a beta-lactam of structure Beta-Lactam I or Beta-Lactam II, wherein $R^1$ represents methyl, and $R^2$ and $R^3$ represent a hydrogen atom.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents pyridinium-yl which optionally has carbamoyl lower alkyl, carboxyl lower alkyl, or aminosulfonylamino lower alkyl at its 1-position and amino lower alkylthio at other position than the 1-position.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents pyridin-3-yl.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carbamoylmethylpyridinium-3-yl.

In other embodiments, the present disclosure relates to a method, composition, or use of a beta-lactam of structure Beta-Lactam I or Beta-Lactam II, wherein $R^1$, $R^2$ and $R^3$ represent a hydrogen atom, n is 0 (zero), and Hy represents 1-carbamoylmethylpyridinium-3-yl.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carbamoylmethyl-5-phenylpyridinium-3-yl.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents (2S)-pyrrolidin-2-yl.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-carboxymethylpyridinium-3-yl.

In other embodiments, the present disclosure relates to a method, composition, or use of a beta-lactam of structure Beta-Lactam I or Beta-Lactam II, wherein $R^1$ represents methyl, $R^2$ and $R^3$ represent a hydrogen atom, n is 0 (zero), and Hy represents 1-(2-aminosulfonylaminoethyl)pyridinium-3-yl.

In other embodiments, the present disclosure relates to a method, composition, or use wherein said beta-lactam or carbapenem corresponds to the following structure:

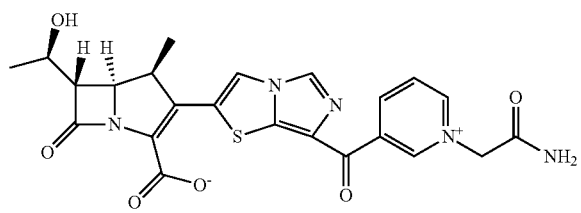 [SMILES: C[C@@H](O)[C@H]1C(=O)N2C(C(=O)[O-])=C(c3cn4cnc(C(=O)c5ccc[n+](CC(N)=O)c5)c4s3)[C@H](C)[C@H]12]

or a pharmaceutically acceptable salt, ester, or prodrug thereof. This foregoing beta-lactam or carbapenem is also known by the publicly disclosed code names ME1036 and CP5609.

Aminomethylcycline Compounds

Aminomethylcycline compounds such as 7-methylamino-9-(2,2-dimethyl-propyl)aminomethylcycline and their pharmaceutically acceptable salts, esters, and prodrugs thereof, can be used in the methods, compositions, and uses of the present disclosure. The compound, 7-methylamino-9-(2,2-dimethyl-propyl)aminomethylcycline, is also known by the publicly disclosed code names PTK 0796 and BAY 73-6944. See U.S. Pat. No. 6,846,939 B2, to Nelson et al., issued Jan. 25, 2005; U.S. Patent Application No. US 2005/0070510 A1, to Draper et al., published Mar. 31, 2005; U.S. Patent Application No. US 2005/0026876 A1, to Nelson et al., published Feb. 3, 2005; U.S. Patent Application No. US 2005/0026875 A1, to Nelson et al., published Feb. 3, 2005;

U.S. Patent Application No. US 2004/0242548 A1, to Draper et al., published Dec. 2, 2004; U.S. Patent Application No. US 2004/0214801 A1, to Nelson et al, published Oct. 28, 2004; U.S. Patent Application No. US 2004/0214800 A1, to Levy et al., published Oct. 28, 2004; U.S. Patent Application No. US 2004/0092490 A1, to Draper et al., published May 13, 2004; U.S. Patent Application No. US 2004/0063674 A1, to Levy et al., published Apr. 1, 2004; U.S. Patent Application No. US 2003/0166585 A1, to Draper et al., published Sep. 4, 2003; U.S. Patent Application No. US 2003/0125348 A1, to Nelson et al, published Jul. 3, 2003; PCT Application No. WO 2005/009944, to Paratek Pharmaceuticals, Inc., published Feb. 3, 2005; PCT Application No. WO 2004/091513, to Paratek Pharmaceuticals, Inc., published Oct. 28, 2004; PCT Application No. WO 2004/064728, to Paratek Pharmaceuticals, Inc., published Aug. 5, 2004; PCT Application No. WO 2004/038001, to Paratek Pharmaceuticals, Inc., published May 6, 2004; PCT Application No. WO 2004/038000, to Paratek Pharmaceuticals, Inc., published May 6, 2004; PCT Application No. WO 03/075857, to Paratek Pharmaceuticals, Inc., published Sep. 18, 2003; PCT Application No. WO 03/005971, to Paratek Pharmaceuticals, Inc., published Jan. 23, 2003; PCT Application No. WO 02/072031, to Paratek Pharmaceuticals, Inc., published Sep. 19, 2002; and PCT Application No. WO 02/04406, to Trustees of Tufts College and Paratek Pharmaceuticals, Inc., published Jan. 17, 2002.

Dalbavancin

Dalbavancin and its pharmaceutically acceptable salts, esters, and prodrugs thereof, can be used in the methods, compositions, and uses of the present disclosure. Dalbavancin, which is a semisynthetic glycopeptide is also known by the publicly disclosed code names VER-001 and BI397. See G. Candiani et al., "In-Vitro and In-Vivo Antibacterial Activity of BI 397, a New Semi-Synthetic Glycopeptide Antibiotic", J. Antimicrob. Chemotherapy, 44, pp. 179-192 (1999); U.S. Patent Application No. US 2005/0090433 A1, to Colombo et al., published Apr. 28, 2005; U.S. Patent Application No. US 2005/0004050 A1, to Stogniew, published Jan. 6, 2005; U.S. Patent Application No. US 2004/0224908 A1, to Cavaleri et al., published Nov. 11, 2004; U.S. Patent Application No. US 2004/0220122 A1, to Cavaleri et al., published Nov. 4, 2004; U.S. Patent Application No. US 2004/0198715 A1, to Cavaleri et al., published Oct. 7, 2004.

Daptomycin

Daptomycin and its pharmaceutically acceptable salts, esters, and prodrugs thereof, can be used in the methods, compositions, and uses of the present disclosure. Daptomycin is sold under the trade name or proprietary Cubicin. See U.S. Pat. No. 6,852,689 B2, to Oleson, Jr. et al., issued Feb. 8, 2005; U.S. Pat. No. 6,468,967 B1, to Oleson, Jr. et al., issued Oct. 22, 2002; and U.S. Pat. No. 5,912,226, to Baker et al., issued Jun. 15, 1999; and PCT Application No. WO 00/18419, to Cubist Pharmaceuticals, Inc., published Apr. 6, 2000.

Oritavancin

Oritavancin and its pharmaceutically acceptable salts, esters, and prodrugs thereof, can be used in the methods, compositions, and uses of the present disclosure. Oritavancin, which is a glycopeptide, is also known by the publicly disclosed code name LY333328. See R. C. Mercier et al., "Pharmacodynamic Evaluation of a New Glycopeptide, LY333328, and In Vitro Activity against *Staphylococcus aureus* and *Enterococcus faecium*", Antimicrobial Agents and Chemotherapy, vol. 41, no. 6, pp. 1307-1312 (June 1997); U.S. Pat. No. 5,998,581, to Berglund et al., issued Dec. 7, 1999 and its certificate of correction of Nov. 14, 2000; U.S. Pat. No. 5,994,297, to Nicas et al., issued Nov. 30, 1999; U.S. Pat. No. 5,977,062, to Cooper et al., issued Nov. 2, 1999; U.S. Pat. No. 5,952,466, to Berglund et al, issued Sep. 14, 1999; U.S. Pat. No. 5,939,382, to Berglund et al., issued Aug. 17, 1999; U.S. Pat. No. 5,843,889, to Cooper et al., issued Dec. 1, 1998 and its certificate of correction of Mar. 28, 2000; U.S. Pat. No. 5,840,684, to Cooper et al., issued Nov. 24, 1998; PCT Application No. WO 00/66144, to Eli Lilly and Company, published Nov. 9, 2000; PCT Application No. WO 99/10006, to Eli Lilly and Company, published Mar. 4, 1999; PCT Application No. WO 98/22121, to Eli Lilly and Company, published May 28, 1998; PCT Application No. WO 98/21952, to Eli Lilly and Company, published May 28, 1998; and PCT Application No. WO 96/30401, to Eli Lilly and Company, published Oct. 3, 1996.

Televancin

Televancin and its pharmaceutically acceptable salts, esters, and prodrugs thereof, can be used in the methods, compositions, and uses of the present disclosure. Televancin, which is a peptidoglycan, can be prepared by the sequential reduction amination of vancomycin and reaction with aminomehtylphosphonic acid. Televancin can also be prepared by the reductive alkylation of vancomycin with N-decyl-N-fluoroenyl-methyloxycarbonyl-2-aminoacetaldehyde via sodium cyano-borohydride and trifluoroacetic acid, and modification of the resorcinol position via Mannich aminomethylation. Televancin can also be prepared from vancomycin or its analogues by the sequential reaction with a protected amino-aldehyde, an amine and then an aminoalkylphosphonic acid in the presence of formaldehyde. See U.S. Pat. No. 6,887,976 B2, to Leadbetter et al., issued May 3, 2005; U.S. Pat. No. 6,878,686 B2, to Marquess et al., issued Apr. 12, 2005; U.S. Pat. No. 6,872,804 B2, to Mu, issued Mar. 29, 2005; U.S. Pat. No. 6,872,701 B2, to Leadbetter et al., issued Mar. 29, 2005; U.S. Pat. No. 6,858,584 B2, to Judice et al., issued Feb. 22, 2005; U.S. Pat. No. 6,831,150 B2, to Linsell, issued Dec. 14, 2004; U.S. Pat. No. 6,828,299 B2, to Yang et al., issued Dec. 7, 2004; U.S. Pat. No. 6,770,621 B2, to Linsell et al., issued Aug. 3, 2004; U.S. Pat. No. 6,635,618 B2, to Leadbetter et al., issued Oct. 21, 2003; U.S. Pat. No. 6,620,781 B2, to Linsell et al., issued Sep. 16, 2003; U.S. Pat. No. 6,518,242 B1, to Chen et al. issued Feb. 11, 2003; and U.S. Pat. No. 6,455,669 B1, to Judice et al., issued Sep. 24, 2002; and PCT Application No. WO 03/029270, to Theravance, Inc., published Apr. 10, 2003.

DK-507k

The compound DK-507k and its pharmaceutically acceptable salts, esters, and prodrugs thereof, can be used in the methods, compositions, and uses of the present disclosure. DK-507k can be described as a fluoroquinolone. DK-507k is also known by the chemical name (−)-7-[(7S)-7-amino-5-azaspiro[2.4]heptan-5-yl]-6-fluoro-1-[(1R,2S)-2-fluoro-1-cyclopropyl]-1,4-dihydro-8-methoxy-4-oxo-3-quinolinecarboxylic acid monohydrochloride monohydrate. See Otani et al., *In Vitro and In Vivo antibacterial Activities of DK-507k, a Novel Fluoroquinolone*, Antimicrobial Agents and Chemotherapy, Vol. 47, no. 12, pages 3750-3759 (2003); Japanese Patent No. JP 2004244380 A2, to Daiichi Seiyaku Co., Ltd., Japan, Sep. 2, 2004; PCT Application No. WO 2004/058261, to Daiichi Pharmaceutical Co., Ltd., Japan, published Jul. 15, 2004; PCT Patent Application No., WO 2003/076248, to Daiichi Pharmaceutical Co., Ltd., Japan, published Sep. 18, 2003; Japanese Patent No. JP 2003096075 A2, to Daiichi Seiyaku Co., Ltd., Japan, Apr. 3, 2003; Japanese Patent No. JP 2002255962 A2, to Daiichi Seiyaku Co., Ltd., Japan, Sep. 11, 2002; Japanese Patent No. JP 2002201191 A2 to Daiichi Seiyaku Co., Ltd., Japan, Jul. 16, 2002; PCT Application No. WO 2001/072738, to Daiichi Pharmaceutical Co., Ltd., Japan, published Oct. 4, 2001; U.S. Pat. No. 6,900,225 B2, to Takemura et al., issued May 31, 2005; U.S. Patent Application No. 2004/142957 A1, to Takemura et al., published Jul. 22, 2004; U.S. Patent Application No. 2003/187008 A1, to Takemura et al., published Oct. 2, 2003; PCT Application No. WO 2001/058876, to Daiichi Pharmaceutical Co., Ltd., Japan, published Aug. 16, 2001; and U.S. Patent Application No. 2003/119848 A1, to Takemura et al., published Jun. 26, 2003.

DK-507k can be represented by the following formula;

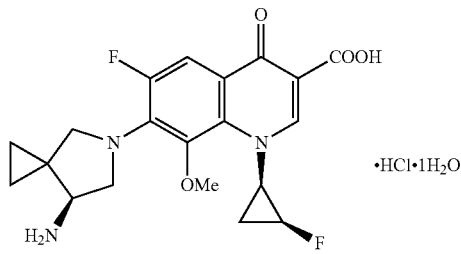 [SMILES: COc1c(N2C[C@@H](N)C3(CC3)C2)c(F)cc2c(=O)c(C(=O)O)cn([C@@H]3C[C@@H]3F)c12]

The compound can also be obtained as crystals exhibiting characteristic peaks in the vicinity of angles of diffraction (2θ) of 6.9, 10.5, 14.4, 23.1, 26.9, and 27.8(°) when subjected to powder X-ray diffractometry.

The anhydrous free acid of the above compound, as well as other salts, esters, and prodrugs, and also hydrates of the compounds can be prepared and used in the present disclosure. Also other crystal forms of the foregoing can be prepared and used in the present disclosure.

Dosing

The methods of the present disclosure are useful for treating, preventing or reducing the risk of infection due to, e.g., a skin infection, nosocomial pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant *Enterococci* infection, a linezolid-resistant organism infection, tuberculosis, a quinolone resistant Gram-positive infection, a ciprofloxacin resistant methicillin resistant (MRSA) infection, bronchitis, a complicated skin and skin structure infection (cSSSI), an uncomplicated skin and skin structure infection (uSSSI), a community respiratory-tract infection, and a multi-drug resistant (MDR) Gram-negative infection.

The dose of active compound and mode of administration, e.g., injection, intravenous drip, etc. will depend upon the intended patient or subject and the targeted microorganism, e.g., the target bacterial organism. Dosing strategies are disclosed in L. S. Goodman, et al., *The Pharmacological Basis of Therapeutics*, 201-26 (5th ed. 1975), the entire contents of which is herein incorporated in its entirety.

Compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, by parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

In conjunction with the methods of the present disclosure, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

The amount administered to a patient will likely depend on such variables as the overall health status of the patient, the relative biological efficacy of the compound delivered, the formulation of the drug, the presence and types of excipients in the formulation, the route of administration, and the infection to be treated, prevented, or reducing the risk of. Also, it is to be understood that the initial dosage administered can be increased beyond the above upper level in order to rapidly achieve the desired blood-level or tissue level, or the initial dosage can be smaller than the optimum.

In some embodiments, the dose of active compound comprises from about 0.1 to about 1500 mg of the compound per dose. In some embodiments, the dose of active compound is selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e. minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

EXAMPLES

The following examples further describe and demonstrate embodiments within the scope of the present disclosure. The examples are given solely for the purpose of illustration and are not to be construed as limitations of the present disclosure, as many variations thereof are possible without departing from the spirit and scope of the disclosure.

Ingredients are identified by chemical, USP, or CTFA name.

The following formulations are preparing using mixing techniques and equipment familiar to one of ordinary skill in the art.

These formulations are useful for intravenous administration, either infusion or bolus, such as injection, to a patient for treating, preventing, or reducing the risk of a microbial infection, e.g., a skin infection, including uncomplicated skin infections, skin and soft tissue infections, complicated skin infections, pneumonia, including e.g., community acquired pneumonia, nosocomial (hospital acquired) pneumonia, hospital acquired community pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant *Enterococci* infection, a linezolid-resistant organism infection, and tuberculosis. More specifically, this formulation is useful for reducing the risk of or preventing infection due to a surgical or invasive medical procedure to be performed upon the patient, and in such case, the formulation can be administered just prior to or up to about 1 hour prior to the surgical or invasive medical procedure.

Example 1

Composition of Delafloxacin-Meglumine Formulation for Intravenous Administration

| Ingredient | Mg/mL | Batch size, mL % (weight/volume) | 1000 gram Batch Amt (g)/batch |
| --- | --- | --- | --- |
| Delafloxacin Meglumine (amount as free acid) | 20.000 | 2.00% | 20.000 |
| Meglumine (anhydrous, mw 195.21) | 4.88 | 0.49% | 4.880 |
| Captisol | 200 | 20.00% | 200 |
| Water for Injection | q.s. | q.s. | q.s. |
| 1 N NaOH and/or HCl acid | q.s. | q.s. | q.s. |
| Density | 1.082 g/ml | | |
| Final pH | 9.0 (±0.1) | | |

API supplied as Meglumine salt of delafloxacin, 28.86 mg/mL Delafloxacin Meglumine salt=20 mg/mL as free base Conversion factor between RX-3341 salt/free acid=1.4429

Volume for 150 mg dose=8 mL

Procedure:
1. Weigh Water for Injection approximately 70% of the total batch weight into a suitable container.
2. Add the required amount of Captisol (beta-Cyclodextrin sulfobutyl ether sodium) to the solution and mix until dissolved.
3. Add the required amount of Meglumine to the solution and mix until dissolved.
4. Add the required amount of delafloxacin corrected for purity and salt content and mix until dissolved.
5. Test for pH. The target pH is 9.0 (0.1).

Adjust with Hydrochloric Acid (as a 1N solution) or Sodium Hydroxide (as a 1N solution) as needed.

6. q.s. to the final weight or volume with Water for Injection.
7. Sterile filter solution (two filters 0.22 um) and fill into vials.

Based on the above foregoing formulation table, the following mg of the indicated component is delivered in a given dosage.

| | 100 mg strength dosage | 300 mg strength dosage | 500 mg strength dosage |
| --- | --- | --- | --- |
| Delafloxacin | 100 mg | 300 mg | 500 mg |
| Meglumine | 24.4 mg | 73.2 mg | 122 mg |
| Captisol | 1000 mg | 3000 mg | 5000 mg |

The foregoing composition is useful for intravenous administration to a patient for treating, preventing, or reducing the risk of a microbial infection.

Example 2

Composition of Delafloxacin-Meglumine Formulation for Intravenous Administration

| Ingredient | Mg/ml | Batch size, mL % (weight/volume) | 1000 gram Batch Amt (g)/batch |
|---|---|---|---|
| Delafloxacin Meglumine (amount as free acid) | 25.000 | 2.50% | 25.000 |
| Meglumine (anhydrous, mw 195.21) | 4.88 | 0.49% | 4.880 |
| Captisol | 200 | 20.00% | 200 |
| Disodium EDTA, 0.1M Solution | 0.11* | 0.011% | 0.11 |
| Water for Injection | q.s. | q.s. | q.s. |
| 1 N NaOH and/or HCl acid | q.s. | q.s. | q.s. |
| Density | 1.087 g/ml | | |
| Final pH | 9.0 (±0.1) | | |

API supplied as Meglumine salt of delafloxacin, 28.86 mg/mL Delafloxacin Meglumine salt=20 mg/mL as free base The disodium EDTA concentration is expressed on a free acid basis.

Conversion factor between delafloxacin salt to free acid is 1.4429

Volume for 150 mg dose=6 mL

Procedure:
1. Weigh Water for Injection approximately 70% of the total batch weight into a suitable container.
2. Add the required amount of Captisol (beta-Cyclodextrin sulfobutyl ether sodium) to the solution and mix until dissolved.
3. Add the required amount of Meglumine to the solution and mix until dissolved.
4 Add the EDTA solution and mix.
5. Add the required amount of delafloxacin corrected for purity and salt content and mix until dissolved.
6. Test for pH. The target pH is 9.0 (0.1).

Adjust with Hydrochloric Acid (as a 1N solution) or Sodium Hydroxide (as a 1N solution) as needed.

7. q.s. to the final weight or volume with Water for Injection.
8. Sterile filter solution (two filters 0.22 um) and fill into vials.

*In further formulations, the amount of EDTA solution add is increased to 0.15 mg/mL.

The foregoing composition is useful for intravenous administration to a patient for treating, preventing, or reducing the risk of a microbial infection.

Based on the above foregoing formulation table, the following mg of the indicated component is delivered in a given dosage.

| | 100 mg strength dosage | 300 mg strength dosage | 500 mg strength dosage |
|---|---|---|---|
| Delafloxacin | 100 mg | 300 mg | 500 mg |
| Meglumine | 19.52 mg | 58.56 mg | 97.6 mg |
| Captisol | 800 mg | 2400 mg | 4000 mg |
| Disodium EDTA | 0.44 mg | 1.32 mg | 2.2 mg |

Example 3

Lyophilisates for Reconstitution for Intravenous Administration

Formulations can also be prepared as lyophilisates. For example, the formulations of Examples 1 and 2, above can also be prepared as lyophiles. This is accomplished by sterile filtering the solutions into lyophile vials, and then freeze drying the vials using conventional freeze drying techniques.

Such formulations are reconstituted with water or another appropriate aqueous based solution. These lyophilisates are a compact and convenient form to store the formulation.

Example 4

Formulations for Oral Administration

| Ingredients | mg/100 mg strength | mg/200 mg strength |
|---|---|---|
| Delafloxacin Meglumine (a) | 144.3 | 288.6 |
| Vitamin E TPGS (b) | 120 | 240 |
| Povidone K-30 | 10 | 20 |
| Arginine | 25 | 50 |
| Microcrystalline Cellulose | 29.2 | 58.4 |
| Water (c) | q.s. | q.s. |
| Mg Stearate | 1.5 | 3 |
| Total | 330 | 660 |

(a) Delafloxacin Meglumine Active Pharmaceutical Ingredient in 144.3 mg = 100 mg free acid
(b) Vitamin E TPGS was melted and incorporated into the formulation as a granulation fluid.
(c) Water was removed during drying process.

Alternatively, other formulations can be made by replacing the microcrystalline cellulose with other fillers such as mannitol, lactose, xylitol, or other materials that can be used as fillers at an approximately equivalent or different weight.

The manufacturing process involves, but is not limited to as described immediately below.

The vitamin E TPGS was melted with mixing in a 55° C. oven to form a uniform melt and the appropriate amount was then weighed into a granulation beaker and held at 40-55° C.

The delafloxacin and the intragranular excipient(s), such as for example, arginine, PVP, microcrystalline cellulose, were weighed into a mixing vessel and mixed using a mechanical mixer.

This mixture was then mixed with the melted vitamin E TPGS and granulated to form a uniform granulation. If necessary, water can be added to help the granulation.

The resulting mixture was then dried at 30-35° C. until dried.

The material was then passed through a screen and collected in a mixing vessel.

This material was mixed with the extragranular excipients (such as magnesium stearate) in a mechanical mixer.

The resulting material was compressed into individual tablets, or alternatively loaded into standard gelatin capsules.

The resulting formulations are useful for oral administration, for treating, preventing, or reducing the risk of a microbial infection in a patient.

Example 5

Formulations for Oral Administration

| Ingredients | mg/100 mg strength | mg/200 mg strength |
|---|---|---|
| Delafloxacin Meglumine (a) | 144.3 | 288.6 |
| Vitamin E TPGS (b) | 120 | 240 |
| Povidone K-30 | 10 | 20 |
| Microcrystalline Cellulose | 29.2 | 58.4 |
| Water (c) | q.s. | q.s. |
| Mg Stearate | 1.5 | 3 |
| Total | 305 | 610 |

(a) Delafloxacin Meglumine Active Pharmaceutical Ingredient in 144.3 mg = 100 mg free acid
(b) Vitamin E TPGS was melted and incorporated into the formulation as a granulation fluid.
(c) Water was removed during drying process.

Alternatively, other formulations can be made by replacing the microcrystalline cellulose with other fillers such as mannitol, lactose, xylitol, or other materials that can be used as fillers at an approximately equivalent or different weight.

The resulting formulation can be manufactured using the same or similar process described above in Example 4.

The resulting formulation is useful for oral administration, for treating, preventing, or reducing the risk of a microbial infection in a patient.

Example 6

Formulations for Oral Administration

| Ingredients | mg/100 mg strength | mg/200 mg strength |
|---|---|---|
| Delafloxacin Meglumine (a) | 144.3 | 288.6 |
| Vitamin E TPGS (b) | 120 | 240 |
| Arginine | 25 | 50 |
| Microcrystalline Cellulose | 29.2 | 58.4 |
| Water (c) | q.s. | q.s. |
| Mg Stearate | 1.5 | 3 |
| Total | 320 | 640 |

(a) Delafloxacin Meglumine Active Pharmaceutical Ingredient in 144.3 mg = 100 mg free acid
(b) Vitamin E TPGS was melted and incorporated into the formulation as a granulation fluid.
(c) Water was removed during drying process.

Alternatively, other formulations can be made by replacing the microcrystalline cellulose with other fillers such as mannitol, lactose, xylitol, or other materials that can be used as fillers at an approximately equivalent or different weight.

The resulting formulation can be manufactured using the same or similar process described above in Example 1.

The resulting formulation is useful for oral administration, for treating, preventing, or reducing the risk of a microbial infection in a patient.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an Acute Bacterial Skin and Skin Structure Infection (ABSSSI) in an overweight or obese patient in need thereof, the method comprising intravenously (IV) administering to the patient 300 mg of delafloxacin or a pharmaceutically acceptable salt, ester, or prodrug thereof, twice a day.

2. The method of claim 1, wherein the overweight or obese patient has a body mass index greater than or equal to 25.

3. The method of claim 2, wherein the overweight or obese patient has a body mass index greater than or equal to 30.

4. The method of claim 3, wherein the overweight or obese patient has a body mass index greater than or equal to 35.

5. The method of claim 4, wherein the overweight or obese patient has a body mass index greater than or equal to 40.

* * * * *